US009937011B2

(12) United States Patent
Yosibash et al.

(10) Patent No.: US 9,937,011 B2
(45) Date of Patent: Apr. 10, 2018

(54) AUTOMATED PATIENT-SPECIFIC METHOD FOR BIOMECHANICAL ANALYSIS OF BONE

(71) Applicant: PERSIMIO LTD, Be'Er Sheva (IL)

(72) Inventors: Zohar Yosibash, Lehavim (IL); Nir Trabelsi, Meitar (IL); Kent Myers, Moscow, ID (US); Charles Milgrom, Moshav Aminadav (IL)

(73) Assignee: PERSIMIO LTD, Be'Er Sheva (IL)

( * ) Notice: Subject to any disclaimer, the term of this patent is extended or adjusted under 35 U.S.C. 154(b) by 0 days.

(21) Appl. No.: 15/027,701

(22) PCT Filed: Oct. 7, 2014

(86) PCT No.: PCT/IL2014/050878
§ 371 (c)(1),
(2) Date: Apr. 7, 2016

(87) PCT Pub. No.: WO2015/052710
PCT Pub. Date: Apr. 16, 2015

(65) Prior Publication Data
US 2016/0242852 A1 Aug. 25, 2016

Related U.S. Application Data

(60) Provisional application No. 61/888,527, filed on Oct. 9, 2013.

(51) Int. Cl.
*G06K 9/00* (2006.01)
*A61B 34/10* (2016.01)
(Continued)

(52) U.S. Cl.
CPC ............ *A61B 34/10* (2016.02); *A61B 5/0037* (2013.01); *A61B 5/055* (2013.01); *A61B 5/4504* (2013.01);
(Continued)

(58) Field of Classification Search
CPC ....... G06T 17/00; G06T 17/20; G06T 7/0012; G06T 19/00; G06T 2200/04; G06Q 50/22;
(Continued)

(56) References Cited

U.S. PATENT DOCUMENTS

| 8,126,234 B1 | 2/2012 | Edwards et al. |
| 2005/0010106 A1* | 1/2005 | Lang ................. A61B 6/469 600/425 |

(Continued)

FOREIGN PATENT DOCUMENTS

WO 2015/052710 A1 4/2015

OTHER PUBLICATIONS

Yosibash et al., Reliable simulations of the human proximal femur by high-order finite element analysis validated by experimental observations, Jun. 2007, Journal of Biomechanics 40 (2007), pp. 3688-3699.*
Trabelsi et al., Validation of subject-specific automated p-FE analysis of the proximal femur, 2008, Journal of Biomechanics 42 (2009), pp. 234-241.*
International Search Report of PCT/IL2014/050878, dated Feb. 9, 2015.

(Continued)

Primary Examiner — Vu Le
Assistant Examiner — Guillermo Rivera-Martinez

(57) ABSTRACT

A computer-implemented method for providing FEA analysis of at least a portion of at least one bone in a patient, the method comprising steps of: providing at least one image of at least a portion of a bone; selecting at least a portion of the bone; automatically performing an FE analysis of the selected portion of the bone; and displaying at least one result of the FE analysis. Bone selection and display of the bone, the selected portion thereof, and the results of the FE analysis occur via a hand-held device, with processing and data storage performed remotely.

16 Claims, 15 Drawing Sheets

(51) Int. Cl.
*G06T 17/20* (2006.01)
*A61B 6/00* (2006.01)
*A61B 5/00* (2006.01)
*A61B 5/055* (2006.01)
*A61B 6/03* (2006.01)
*G06F 17/50* (2006.01)
*G06T 19/20* (2011.01)

(52) U.S. Cl.
CPC .......... *A61B 5/4884* (2013.01); *A61B 5/7275* (2013.01); *A61B 6/032* (2013.01); *A61B 6/505* (2013.01); *A61B 6/5217* (2013.01); *A61B 6/5258* (2013.01); *G06F 17/5009* (2013.01); *G06T 17/20* (2013.01); *G06T 19/20* (2013.01); *A61B 2034/102* (2016.02); *G06T 2200/04* (2013.01)

(58) Field of Classification Search
CPC ....... B29L 2031/7532; B29L 2031/753; G06F 17/5018
See application file for complete search history.

(56) References Cited

U.S. PATENT DOCUMENTS

| | | | |
|---|---|---|---|
| 2006/0069318 A1* | 3/2006 | Keaveny | A61B 5/4509 600/300 |
| 2006/0290695 A1* | 12/2006 | Salomie | G06T 17/20 345/420 |
| 2007/0118243 A1* | 5/2007 | Schroeder | B33Y 50/00 700/118 |
| 2011/0087465 A1* | 4/2011 | Mahfouz | G06F 19/3437 703/1 |
| 2011/0208033 A1* | 8/2011 | Nicolella | A61B 5/103 600/407 |
| 2011/0259076 A1* | 10/2011 | Faulkner | A61B 5/11 73/1.01 |
| 2013/0211531 A1* | 8/2013 | Steines | A61F 2/4684 623/20.35 |

OTHER PUBLICATIONS

International Search Authority Written Opinion PCT/IL2014/050878, dated Feb. 9, 2015.

* cited by examiner

AUTOMATED PATIENT-SPECIFIC METHOD FOR BIOMECHANICAL ANALYSIS OF BONE

FIELD OF THE INVENTION

The present invention generally pertains to a system and method for using finite element analysis of models of a patient's bone under physiological loading to indicate likely outcome for the patient.

BACKGROUND OF THE INVENTION

Bone endures large stresses from habitual and sporadic loading. Under normal circumstances, bone will withstand these stresses without damage. However, if the bone is weak (e.g. from osteoporosis) or damaged (e.g. from tumors invading the bone wall or preexisting fractures), or if a portion of the bone is to be replaced by an implant, the bone or remaining bone may be too weak to withstand these stresses. Therefore, a biomechanical analysis of the bone (or bone-implant system) can be a valuable aid in deciding the best future course of treatment for the patient. For example, if the bone is likely to fracture under the stresses of normal living, more aggressive treatment of osteoporosis would be indicated. For another example, analysis could indicate whether an implant or pinning is required after removal of a tumor invading the bone wall, or whether bone cement would be sufficient, or, possibly, that no structural infill is needed to retain the structural integrity of the bone.

In the case of replacing a portion of the bone by an implant, implants sometimes fail or loosen and sometimes this leads to fracture of the bone to which they are attached. Biomechanical analysis of a bone-implant system could be used clinically to improve surgical planning. The information derived from such analyses could aid the surgeon in choosing an optimal size and position of a given implant design for a particular patient, or even choose among different implant designs.

Biomechanical analysis could also be used during the design of implants to improve the design, by providing in-computer analysis of the response of both the bone and the implant in bone-implant systems. At the design stage, both patient-specific and generic bones can be used for the in-computer analysis whereas, at the clinical stage, patient-specific bones are preferable.

However, a system such as described above requires software capable of automatically transforming an image of the bone, such as a CT scan, into a finite element (FE) mesh, and of automatically analyzing the stresses, strains and displacements which are the result of a finite element analysis (FEA) in order to provide the clinician with the information he needs—the likelihood of success or failure of a specific intervention.

U.S. Pat. No. 8,126,234 to Edwards discloses to a method and system for orthopaedic surgical planning and more specifically to surgical planning based on an automated FEA of a bone-implant system using a 3D medical image of a patient. However, U.S. Pat. No. 8,126,234 requires the use of a mask for generating the finite element mesh, whereas no mask is needed in the method of the present invention. Furthermore, the FE mesh of U.S. Pat. No. 8,126,234 is generated by overlaying the mask described hereinabove with a predetermined FE mesh which includes both the implant and the bone, whereas, in the present method, the bone mesh is determined ab initio for each bone analyzed.

Furthermore, U.S. Pat. No. 8,126,234 is based on pre-meshed non-patient-specific models that are made patient specific by adding layers of elements where they are needed. It is claimed in U.S. Pat. No. 8,126,234 that to mesh ab initio for each individual patient from captured geometry requires too much FEA expertise and is too time consuming. Because of the high degree of variability of bone geometry in the population, for ab initio meshing, human intervention would be required to adjust the mesh to avoid badly distorted elements. Therefore, these problems make it infeasible to use the method of U.S. Pat. No. 8,126,234 in a clinical setting.

According to U.S. Pat. No. 8,126,234, fully automatic meshing ab initio results in meshed models containing a large enough number of low-order finite elements that solving such meshes becomes infeasible on the timescales required in a clinical context.

It should be noted that although in U.S. Pat. No. 8,126,234 the material properties are estimated from the grey scale of the scan, no details are given of the process by which they are determined. Care must be taken in converting grey scale data to material properties, as inaccurate material properties can invalidate the results.

Furthermore, U.S. Pat. No. 8,126,234 does not address the numerical accuracy of the results, nor the validation of these by past experiments, or describe any means by which errors can be assessed or controlled.

In addition, I/O for U.S. Pat. No. 812,623 is via a conventional terminal or monitor.

It is therefore a long felt need to provide a fully-automatic system that can accept an image of a bone, extract therefrom the bone's shape in three dimensions and the bone's density as a function of position in three dimensions, create and analyze strains/stresses on the physiologically-loaded bone, with or without implants or other surgical modifications, assuring the accuracy of the results while accepting input and displaying results on a hand-held device.

SUMMARY OF THE INVENTION

It is an object of the present invention to disclose a fully-automatic computer-implemented system that can accept an image of a bone, extract therefrom the bone's shape in three dimensions and the bone's density as a function of position in three dimensions, create and analyze strains/stresses on the physiologically-loaded bone, with or without implants or other surgical modifications and assess the numerical accuracy, while accepting input and displaying results on a hand-held device, and to provide a method of using the system.

It is another object of the present invention to disclose a computer-implemented method for providing FEA analysis of at least a portion of at least one bone in a patient, said method comprising steps of:
a. providing at least one image of at least a portion of said bone;
b. selecting at least a portion of said bone;
c. automatically performing an FE analysis of said selected portion of said bone;
d. displaying at least one result of said FE analysis
wherein said steps of selecting and displaying occur via a hand-held device and further wherein at least one of processing and data storage are performed remotely.

It is another object of the present invention to disclose the computer-implemented method, additionally comprising steps of selecting said hand-held device from a group consisting of an IPad, an IPod, a smartphone, a smart watch, a laptop, a notebook, a netbook, a webbook, a desktop PC, a monitor, a tablet PC, a Slate PC, a Pad PC, a television, and any combination thereof.

It is another object of the present invention to disclose the computer-implemented method, additionally comprising steps of storing said data by a method selected from a group consisting of storing said data on a specified computer, storing said data on a specified storage medium, storing said data on a device attached to a specified network, storing said data on a distributed network, and any combination thereof.

It is another object of the present invention to disclose the computer-implemented method, comprising steps of performing said processing on at least one selected from a group consisting of a specified computer, a device attached to a specified network, and a distributed network.

It is another object of the present invention to disclose the computer-implemented method, additionally comprising steps of generating said at least one image by a method selected from a group consisting of: CT, X-ray vector radiography (XVR), MRI, PET, and any combination thereof.

It is another object of the present invention to disclose the computer-implemented method, wherein said steps of performing said FE analysis comprise at least one selected from a group consisting of:
a. determining material properties of said selected portion of said bone as a function of 3D position within said selected portion of said bone;
b. automatically generating a solid model of said selected portion of said bone;
c. automatically generating an FE model of said selected portion of said bone from at least one of said image of said bone and said solid model;
d. automatically applying said material properties to said FE model;
e. automatically applying boundary conditions to said FE model; and
f. automatically analyzing said FE model.

It is another object of the present invention to disclose the computer-implemented method, additionally comprising at least one selected from a group consisting of: displaying an image of at least a portion of said at least one bone; manipulating said bone image; displaying an image of said solid model; manipulating said solid model image; modifying said solid model; displaying an image of said FE mesh; manipulating said FE image; modifying said FE mesh; displaying an image of said bone density; manipulating said density image; modifying said density; displaying said member of said group consisting of loads and constraints; modifying at least one member of said group consisting of loads and constraints; displaying said results of said solution; and manipulating said display of said results.

It is another object of the present invention to disclose the computer-implemented method, wherein said empirically-determined material properties are inhomogeneous.

It is another object of the present invention to disclose the computer-implemented method, wherein said empirically-determined material properties are isotropic, anisotropic and any combination thereof.

It is another object of the present invention to disclose the computer-implemented method, wherein said steps of applying at least one boundary condition comprise applying at least one member of a group consisting of loads and constraints.

It is another object of the present invention to disclose the computer-implemented method, wherein said steps of applying at least one boundary condition comprise applying at least one physiological load.

It is another object of the present invention to disclose the computer-implemented method, additionally comprising steps of:
a. estimating the numerical error in the solved FE model;
b. determining an error criterion from said numerical error;
c. comparing said error criterion to a predetermined limit;
d. if said error criterion is greater than said predetermined limit,
    i. increasing the p-order for the solution; and
    ii. re-solving the FE model using said higher p-order; and
e. repeating steps a-d until said error criterion is smaller than said predetermined limit.

It is another object of the present invention to disclose the computer-implemented method, additionally comprising steps of adding to said analyzable model at least one implant, said steps of adding said implant comprising: providing a database comprising at least one FE mesh of at least one implant; positioning said at least one FE mesh of said at least one implant with respect to said FE mesh of said analyzable model; and connecting said FE mesh of said implant to said FE mesh of said analyzable model such that said connection models the physical connection between said implant and said bone.

It is another object of the present invention to disclose the computer-implemented method, additionally comprising steps of including in said database at least one solid model of said at least one implant.

It is another object of the present invention to disclose the computer-implemented method, additionally comprising steps of positioning said at least one solid model of said at least one implant with respect to said solid model of said analyzable model; positioning of said FE mesh of said implant defined by said positioning of said solid model.

It is another object of the present invention to disclose the computer-implemented method, additionally comprising steps of removing a portion of said FE mesh of said bone.

It is another object of the present invention to disclose the computer-implemented method, additionally comprising steps of removing said FE mesh of said bone automatically.

It is another object of the present invention to disclose the computer-implemented method, additionally comprising steps of removing a portion of said solid model of said bone.

It is another object of the present invention to disclose the computer-implemented method, additionally comprising steps of removing said solid model of said bone automatically.

It is another object of the present invention to disclose the computer-implemented method, additionally comprising steps of selecting said portion of said FE model to be removed to be said portion of said FE model corresponding to said removed portion of said solid model.

It is another object of the present invention to disclose the computer-implemented method, additionally comprising steps of generating said results by analyzing said solved model.

It is another object of the present invention to disclose the computer-implemented method, wherein said steps of analyzing said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

It is another object of the present invention to disclose the computer-implemented method, additionally comprising steps selected from labeling, marking and any combination thereof a member of a group consisting of: a region in said solved model in which at least one of group consisting of at least one stress, at least one strain, at least one function a measure of strains/stresses or any function of these is greater than a predetermined maximum; a region in said solved model where fractures have occurred; a region in said solved model in which movement is greater than a predetermined maximum; and any combination thereof.

It is another object of the present invention to disclose the computer-implemented method, additionally comprising steps of displaying said solved model including said label, said marking and any combination thereof.

It is another object of the present invention to disclose the computer-implemented method, additionally comprising steps of manipulating said solved model including said label, said marking and any combination thereof.

It is another object of the present invention to disclose the computer-implemented method, wherein said steps of determining material properties comprise additional steps of identifying the cortical-trabecular boundary of said bone.

It is another object of the present invention to disclose the computer-implemented method, additionally comprising steps of identifying voxel values of HU>475 ($\rho_{ash}$>0.486 g/cm$^3$) as said cortical bone and identifying voxel values of HU<475 as said trabecular bone.

It is another object of the present invention to disclose a computer-implemented method for providing FEA analysis of at least a portion of at least one bone in a patient, said method comprising:
a. providing at least one image of at least a portion of said bone;
b. calculating material properties of said bone as a function of 3D position within said bone from density of said bone as a function of 3D position within said bone via empirically-determined material properties correlated to density, said density determined from at least one property of said image of said bone;
c. generating an analyzable model using steps of:
  i. generating by an automatic algorithm from said image a solid model of said at least a portion of said at least one bone by steps of: identifying the boundaries of said bone in said image, said boundary identification via edge detection software; smoothing said boundaries; generating a point cloud model of said boundaries; generating spline curves through points in said point cloud; and generating a solid model through said spline curves;
  ii. automatically generating, from said solid model, a FE mesh of said at least a portion of said at least one bone, said FE being p-FE (p-FE) having smooth surfaces;
  iii. applying a noise reduction algorithm by boundary correction and moving average for each said FE in said p-FE mesh;
  iv. for each said FE in said p-FE mesh, setting said material properties of said FE according to said material properties of said bone at said 3D position;
  v. applying boundary conditions to at least one said FE in said FE mesh;
d. solving said analyzable model, thereby generating a solved model; and
e. providing to a user at least one result from said solved model wherein said steps of providing said bone image ensure that said solved model is patient-specific; further wherein said steps of generating said point cloud and generating said spline curves enable the surface of said solid model to be smooth, thereby enabling the surface of said FE model to be smooth, and further wherein said steps of generating said FE mesh of p-FE enable said FEs to have heterogeneous material properties, thereby reducing the number of FEs in said FE mesh.

It is another object of the present invention to disclose the computer-implemented method, additionally comprising steps of storing said data by a method selected from a group consisting of storing said data on a specified computer, storing said data on a specified storage medium, storing said data on a device attached to a specified network, storing said data on a distributed network, and any combination thereof.

It is another object of the present invention to disclose the computer-implemented method, additionally comprising steps of performing said processing on at least one selected from a group consisting of a specified computer, a device attached to a specified network, and a distributed network.

It is another object of the present invention to disclose the computer-implemented method, additionally comprising steps of generating said at least one image by a method selected from a group consisting of: CT, X-ray vector radiography (XVR), MRI, PET, and any combination thereof.

It is another object of the present invention to disclose the computer-implemented method, additionally comprising steps of providing a GUI for display of material related to said image, said outer boundary, said analyzable model, said solved model, said results and any combination thereof.

It is another object of the present invention to disclose the computer-implemented method, additionally comprising at least one selected from a group consisting of: displaying an image of at least a portion of said at least one bone; manipulating said bone image; displaying an image of said solid model; manipulating said solid model image; modifying said solid model; displaying an image of said FE mesh; manipulating said FE image; modifying said FE mesh; displaying an image of said bone density; manipulating said density image; modifying said density; displaying said member of said group consisting of loads and constraints; modifying at least one member of said group consisting of loads and constraints; displaying said results of said solution; and manipulating said display of said results.

It is another object of the present invention to disclose the computer-implemented method, additionally comprising steps of providing said GUI on a hand-held display unit.

It is another object of the present invention to disclose the computer-implemented method, additionally comprising steps of selecting said hand-held display unit from a group consisting of a smartphone, a smart watch, a laptop, a notebook, a netbook, a webbook, a desktop PC, a monitor, a tablet PC, a Slate PC, a Pad PC, a television, and any combination thereof.

It is another object of the present invention to disclose the computer-implemented method, wherein said steps of determining material properties comprise additional steps of identifying the cortical-trabecular boundary of said bone.

It is another object of the present invention to disclose the computer-implemented method, additionally comprising steps of identifying voxel values of HU>475 ($\rho_{ash}$>0.486 g/cm$^3$) as said cortical bone and identifying voxel values of HU<475 as said trabecular bone.

It is another object of the present invention to disclose the computer-implemented method, wherein said empirically-determined material properties are inhomogeneous.

It is another object of the present invention to disclose the computer-implemented method, wherein said empirically-determined material properties are isotropic, anisotropic and any combination thereof.

It is another object of the present invention to disclose the computer-implemented method, wherein said steps of applying at least one boundary condition comprises applying at least one member of a group consisting of loads and constraints.

It is another object of the present invention to disclose the computer-implemented method, wherein said steps of applying at least one boundary condition comprises applying at least one physiological load.

It is another object of the present invention to disclose the computer-implemented method, additionally comprising steps of:
a. estimating the numerical error in the solved FE model;
b. determining an error criterion from said numerical error;
c. comparing said error criterion to a predetermined limit;
d. if said error criterion is greater than said predetermined limit,
   i. increasing the p-order for the solution; and
   ii. re-solving the FE model using said higher p-order; and
e. repeating steps a-d until said error criterion is smaller than said predetermined limit.

It is another object of the present invention to disclose the computer-implemented method, additionally comprising steps of adding to said analyzable model at least one implant, said steps of adding said implant comprising: providing a database comprising at least one FE mesh of at least one implant; positioning said at least one FE mesh of said at least one implant with respect to said FE mesh of said analyzable model; and connecting said FE mesh of said implant to said FE mesh of said analyzable model such that said connection models the physical connection between said implant and said bone.

It is another object of the present invention to disclose the computer-implemented method, additionally comprising steps of including in said database at least one solid model of said at least one implant.

It is another object of the present invention to disclose the computer-implemented method, additionally comprising steps of positioning said at least one solid model of said at least one implant with respect to said solid model of said analyzable model; positioning of said FE mesh of said implant defined by said positioning of said solid model.

It is another object of the present invention to disclose the computer-implemented method, additionally comprising steps of removing a portion of said FE mesh of said bone.

It is another object of the present invention to disclose the computer-implemented method, additionally comprising steps of removing said FE mesh of said bone automatically.

It is another object of the present invention to disclose the computer-implemented method, additionally comprising steps of removing a portion of said solid model of said bone.

It is another object of the present invention to disclose the computer-implemented method, additionally comprising steps of removing said solid model of said bone automatically.

It is another object of the present invention to disclose the computer-implemented method, additionally comprising steps of selecting said portion of said FE model to be removed to be said portion of said FE model corresponding to said removed portion of said solid model.

It is another object of the present invention to disclose the computer-implemented method, additionally comprising steps of generating said results by analyzing said solved model.

It is another object of the present invention to disclose the computer-implemented method, wherein said analyzing of said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

It is another object of the present invention to disclose the computer-implemented method, additionally comprising steps selected from labeling, marking and any combination thereof a member of a group consisting of: a region in said solved model in which at least one of group consisting of at least one stress, at least one strain, at least one function a measure of strains/stresses or any function of these is greater than a predetermined maximum; a region in said solved model where fractures have occurred; a region in said solved model in which movement is greater than a predetermined maximum; and any combination thereof.

It is another object of the present invention to disclose the computer-implemented method, additionally comprising steps of displaying said solved model including said label, said marking and any combination thereof.

It is another object of the present invention to disclose the computer-implemented method, additionally comprising steps of manipulating said solved model including said label, said marking and any combination thereof.

It is another object of the present invention to disclose a computer-implemented system for providing FEA analysis of at least a portion of at least one bone in a patient, said system comprising:
a. a processor adapted to:
   i. select at least a portion of an image of at least a portion of said bone; and
   ii. automatically perform an FE analysis of said selected portion of said bone; and
b. a display device adapted to enable selection of said least a portion of said image of said bone and further adapted to display results of said FE analysis at least one of said wherein said display device is a handheld device and further wherein at least one of processing and data storage are performed remotely.

It is another object of the present invention to disclose the computer-implemented system, wherein said hand-held device is selected from a group consisting of an IPad, an IPod, a smartphone, a smart watch, a laptop, a notebook, a netbook, a webbook, a desktop PC, a monitor, a tablet PC, a Slate PC, a Pad PC, a television, and any combination thereof.

It is another object of the present invention to disclose the computer-implemented system, wherein said data is stored by a method selected from a group consisting of storing said data on a specified computer, storing said data on a specified storage medium, storing said data on a device attached to a specified network, storing said data on a distributed network, and any combination thereof.

It is another object of the present invention to disclose the computer-implemented system, wherein said processing is performed on at least one selected from a group consisting of a specified computer, a device attached to a specified network, and a distributed network.

It is another object of the present invention to disclose the computer-implemented system, wherein said at least one image is generated by a method selected from a group consisting of: CT, X-ray vector radiography (XVR), MRI, PET, and any combination thereof.

It is another object of the present invention to disclose the computer-implemented system, wherein said FE analysis is adapted to perform at least one selected from a group consisting of:
a. determine material properties of said selected portion of said bone as a function of 3D position within said selected portion of said bone;
b. automatically generate a solid model of said selected portion of said bone;
c. automatically generate an FE model of said selected portion of said bone from at least one of said image of said bone and said solid model;
d. automatically apply said material properties to said FE model;
e. automatically apply boundary conditions to said FE model; and
f. automatically analyze said FE model.

It is another object of the present invention to disclose the computer-implemented system, additionally adapted to perform at least one selected from a group consisting of: display an image of at least a portion of said at least one bone; manipulate said bone image; display an image of said solid model; manipulate said solid model image; modify said solid model; display an image of said FE mesh; manipulate said FE image; modify said FE mesh; display an image of said bone density; manipulate said density image; modify said density; display said member of said group consisting of loads and constraints; modify at least one member of said group consisting of loads and constraints; display said results of said solution; and manipulate said display of said results.

It is another object of the present invention to disclose the computer-implemented system, wherein said empirically-determined material properties are inhomogeneous.

It is another object of the present invention to disclose the computer-implemented system, wherein said empirically-determined material properties are isotropic, anisotropic and any combination thereof.

It is another object of the present invention to disclose the computer-implemented system, wherein applying said at least one boundary condition comprises applying at least one member of a group consisting of loads and constraints.

It is another object of the present invention to disclose the computer-implemented system, wherein applying said at least one boundary condition comprises applying at least one physiological load.

It is another object of the present invention to disclose the computer-implemented system, additionally adapted to:
a. estimate the numerical error in the solved FE model;
b. determine an error criterion from said numerical error;
c. compare said error criterion to a predetermined limit;
d. if said error criterion is greater than said predetermined limit,
  i. increase the p-order for the solution; and
  ii. re-solve the FE model using said higher p-order; and
e. repeat steps a-d until said error criterion is smaller than said predetermined limit.

It is another object of the present invention to disclose the computer-implemented system, additionally adapted to add to said analyzable model at least one implant, said addition of said implant comprising: providing a database comprising at least one FE mesh of at least one implant; positioning said at least one FE mesh of said at least one implant with respect to said FE mesh of said analyzable model; and connecting said FE mesh of said implant to said FE mesh of said analyzable model such that said connection models the physical connection between said implant and said bone.

It is another object of the present invention to disclose the computer-implemented system, wherein said database includes at least one solid model of said at least one implant.

It is another object of the present invention to disclose the computer-implemented system, additionally adapted to position said at least one solid model of said at least one implant with respect to said solid model of said analyzable model; positioning of said FE mesh of said implant defined by said positioning of said solid model.

It is another object of the present invention to disclose the computer-implemented system, additionally adapted to remove a portion of said FE mesh of said bone.

It is another object of the present invention to disclose the computer-implemented system, additionally adapted to remove said FE mesh of said bone automatically.

It is another object of the present invention to disclose the computer-implemented system, additionally adapted to remove a portion of said solid model of said bone.

It is another object of the present invention to disclose the computer-implemented system, additionally adapted to remove said solid model of said bone automatically.

It is another object of the present invention to disclose the computer-implemented system, additionally adapted to select said portion of said FE model to be removed to be said portion of said FE model corresponding to said removed portion of said solid model.

It is another object of the present invention to disclose the computer-implemented system, additionally adapted to generate said results by analyzing said solved model.

It is another object of the present invention to disclose the computer-implemented system, wherein said analysis of said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

It is another object of the present invention to disclose the computer-implemented system, additionally adapted to perform at least one selected from labeling, marking and any combination thereof a member of a group consisting of: a region in said solved model in which at least one of group consisting of at least one stress, at least one strain, at least one function a measure of strains/stresses or any function of these is greater than a predetermined maximum; a region in said solved model where fractures have occurred; a region in said solved model in which movement is greater than a predetermined maximum; and any combination thereof.

It is another object of the present invention to disclose the computer-implemented system, additionally adapted to display said solved model including said label, said marking and any combination thereof.

It is another object of the present invention to disclose the computer-implemented system, additionally adapted to manipulate said solved model including said label, said marking and any combination thereof.

It is another object of the present invention to disclose the computer-implemented system, additionally adapted to identify the cortical-trabecular boundary of said bone.

It is another object of the present invention to disclose the computer-implemented system, wherein voxel values of HU>475 ($\rho_{ash}$>0.486 g/cm$^3$) identify said bone as said cortical bone and voxel values of HU<475 identify said bone as said trabecular bone.

It is another object of the present invention to disclose a computer-implemented system for providing FEA analysis of at least a portion of at least one bone in a patient, said system comprising:

a. at least one processor adapted to:
  i. input an image of at least a portion of at least one bone in a patient;
  ii. calculate material properties of said bone as a function of 3D position within said bone from density of said bone as a function of 3D position within said bone via empirically-determined inhomogeneous isotropic material properties correlated to density, said density determined from at least one property of said image of said bone;
  iii. generate an analyzable model, said generation comprising:
    1. generation by an automatic algorithm, from said image, of a solid model of said at least a portion of said at least one bone by identifying the boundaries of said bone in said image, said boundary identification via edge detection software; smoothing said boundaries; creating a point cloud model of said boundaries; generating spline curves through points in said point cloud; and generating a solid model through said spline curves;
    2. automatic generation, from said solid model, of a FE mesh of said at least a portion of said at least one bone, said FEs being p FEs (p-FE);
    3. for each said FE in said p-FE mesh, setting of said material properties of said FE according to said material properties of said bone at said 3D position; and
    4. application of at least one member of a group consisting of loads and constraints to at least one said FE in said FE mesh;
  iv. solve said analyzable model, thereby generating a solved model; and
b. a means of providing to a user at least one result from said solved model wherein said bone image enables said solved model to be patient-specific; further wherein said point cloud and spline curves enable the surface of said solid model to be smooth, and further wherein said use of said p-FEs enables said FEs to have heterogeneous material properties and reduce the number of FEs in said FE mesh.

It is another object of the present invention to disclose the computer-implemented system, wherein said data are stored by a method selected from a group consisting of storing said data on a specified computer, storing said data on a specified storage medium, storing said data on a device attached to a specified network, storing said data on a distributed network, and any combination thereof.

It is another object of the present invention to disclose the computer-implemented system, wherein said processing is performed on at least one selected from a group consisting of a specified computer, a device attached to a specified network, and a distributed network.

It is another object of the present invention to disclose the computer-implemented system, wherein said at least one image is generated by a method selected from a group consisting of: CT, X-ray vector radiography (XVR), MRI, PET, and any combination thereof.

It is another object of the present invention to disclose the computer-implemented system, wherein a GUI is provided for display of material related to said image, said outer boundary, said analyzable model, said solved model, said results and any combination thereof.

It is another object of the present invention to disclose the computer-implemented system, additionally adapted to perform at least one selected from a group consisting of: display an image of at least a portion of said at least one bone; manipulate said bone image; display an image of said solid model; manipulate said solid model image; modify said solid model; display an image of said FE mesh; manipulate said FE image; modify said FE mesh; display an image of said bone density; manipulate said density image; modify said density; display said member of said group consisting of loads and constraints; modify at least one member of said group consisting of loads and constraints; display said results of said solution; and manipulate said display of said results.

It is another object of the present invention to disclose the computer-implemented system, wherein said GUI is provided on a hand-held display unit.

It is another object of the present invention to disclose the computer-implemented system, wherein said hand-held display unit is selected from a group consisting of a smartphone, a smart watch, a laptop, a notebook, a netbook, a webbook, a desktop PC, a monitor, a tablet PC, a Slate PC, a Pad PC, a television, and any combination thereof.

It is another object of the present invention to disclose the computer-implemented system, wherein said steps of identifying boundaries comprise additional steps of identifying the cortical-trabecular boundary of said bone.

It is another object of the present invention to disclose the computer-implemented system, wherein voxel values of HU>475 ($\rho_{ash}$>0.486 g/cm$^3$) identify said bone as said cortical bone and voxel values of HU<475 identify said bone as said trabecular bone.

It is another object of the present invention to disclose the computer-implemented system, wherein said empirically-determined material properties are inhomogeneous.

It is another object of the present invention to disclose the computer-implemented system, wherein said empirically-determined material properties are isotropic, anisotropic and any combination thereof.

It is another object of the present invention to disclose the computer-implemented system, wherein applying said at least one boundary condition comprises applying at least one member of a group consisting of loads and constraints.

It is another object of the present invention to disclose the computer-implemented system, wherein applying said at least one boundary condition comprises applying at least one physiological load.

It is another object of the present invention to disclose the computer-implemented system, additionally adapted to:
a. estimate the numerical error in the solved FE model;
b. determine an error criterion from said numerical error;
c. compare said error criterion to a predetermined limit;
d. if said error criterion is greater than said predetermined limit,
  i. increase the p-order for the solution; and
  ii. re-solve the FE model using said higher p-order; and
e. repeat steps a-d until said error criterion is smaller than said predetermined limit.

It is another object of the present invention to disclose the computer-implemented system, additionally adapted to add to said analyzable model at least one implant, said addition of said implant comprising: providing a database comprising at least one FE mesh of at least one implant; positioning said at least one FE mesh of said at least one implant with respect to said FE mesh of said analyzable model; and connecting said FE mesh of said implant to said FE mesh of said analyzable model such that said connection models the physical connection between said implant and said bone.

It is another object of the present invention to disclose the computer-implemented system, wherein said database includes at least one solid model of said at least one implant.

It is another object of the present invention to disclose the computer-implemented system, additionally adapted to position said at least one solid model of said at least one implant with respect to said solid model of said analyzable model; positioning of said FE mesh of said implant defined by said positioning of said solid model.

It is another object of the present invention to disclose the computer-implemented system, additionally adapted to remove a portion of said FE mesh of said bone.

It is another object of the present invention to disclose the computer-implemented system, additionally adapted to remove said FE mesh of said bone automatically.

It is another object of the present invention to disclose the computer-implemented system, additionally adapted to remove a portion of said solid model of said bone.

It is another object of the present invention to disclose the computer-implemented system, additionally adapted to remove said solid model of said bone automatically.

It is another object of the present invention to disclose the computer-implemented system, additionally adapted to select said portion of said FE model to be removed to be said portion of said FE model corresponding to said removed portion of said solid model.

It is another object of the present invention to disclose the computer-implemented system, additionally adapted to generate said results by analyzing said solved model.

It is another object of the present invention to disclose the computer-implemented system, wherein said analysis of said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

It is another object of the present invention to disclose the computer-implemented system, additionally adapted to perform at least one selected from labeling, marking and any combination thereof a member of a group consisting of: a region in said solved model in which at least one of group consisting of at least one stress, at least one strain, at least one function a measure of strains/stresses or any function of these is greater than a predetermined maximum; a region in said solved model where fractures have occurred; a region in said solved model in which movement is greater than a predetermined maximum; and any combination thereof.

It is another object of the present invention to disclose the computer-implemented system, additionally adapted to display said solved model including said label, said marking and any combination thereof.

It is another object of the present invention to disclose the computer-implemented system, additionally adapted to manipulate said solved model including said label, said marking and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for using finite element analysis (FEA) of models of a patient's bone under physiological loading to determine likely outcome for the patient.

The present invention comprises a system and method for predicting the mechanical response of patient-specific long bones (femurs, humerus, metatarsal, etc), including the estimation of risk of fracture for "as-is" situations or bones that are fixed by implants. The mechanical response is found from stress analysis of bones or portions of bones, with or without implants, bone grafts or other surgical interventions, with the bones and implants (if used) subject to the expected physiological loading. The stress analysis is intended to provide a surgeon or other physician with results useful for informing decisions on patient treatment such as, but not limited to, the size of implant to use, the type of implant to use, whether the bone is strong enough to accept an implant, and whether removal of a portion of the bone will unacceptably weaken the bone. Other uses of such a system will be obvious to those skilled in the art.

In the system of the present invention, the I/O and display are performed via a hand-held device such as a cellular phone, ipads or the like, so that the bone and implant data (if used) can be stored on a remote database and retrieved therefrom and manipulated on the hand-held device. The computations can be performed on a remote CPU, and the results of the computation retrieved therefrom to the hand-held device for examination.

In order to determine bone stresses, an image of the bone in electronic format needs to be made using an appropriate imaging system, as described hereinbelow.

Figure 1:
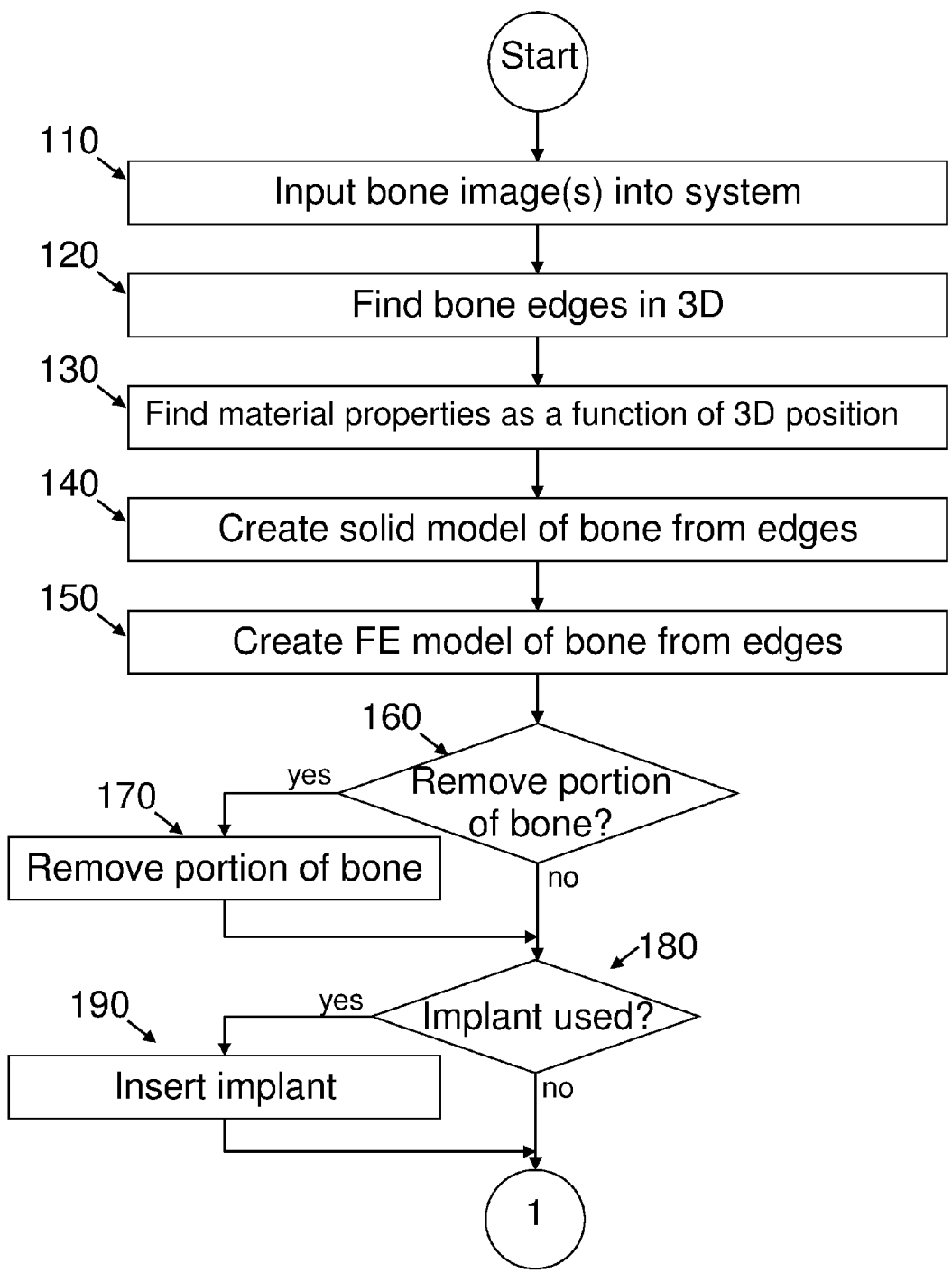
FIGS. 1 and 2 illustrate an embodiment of a flow chart of a method of processing the bone image data to produce results for a user.
Figure 2:
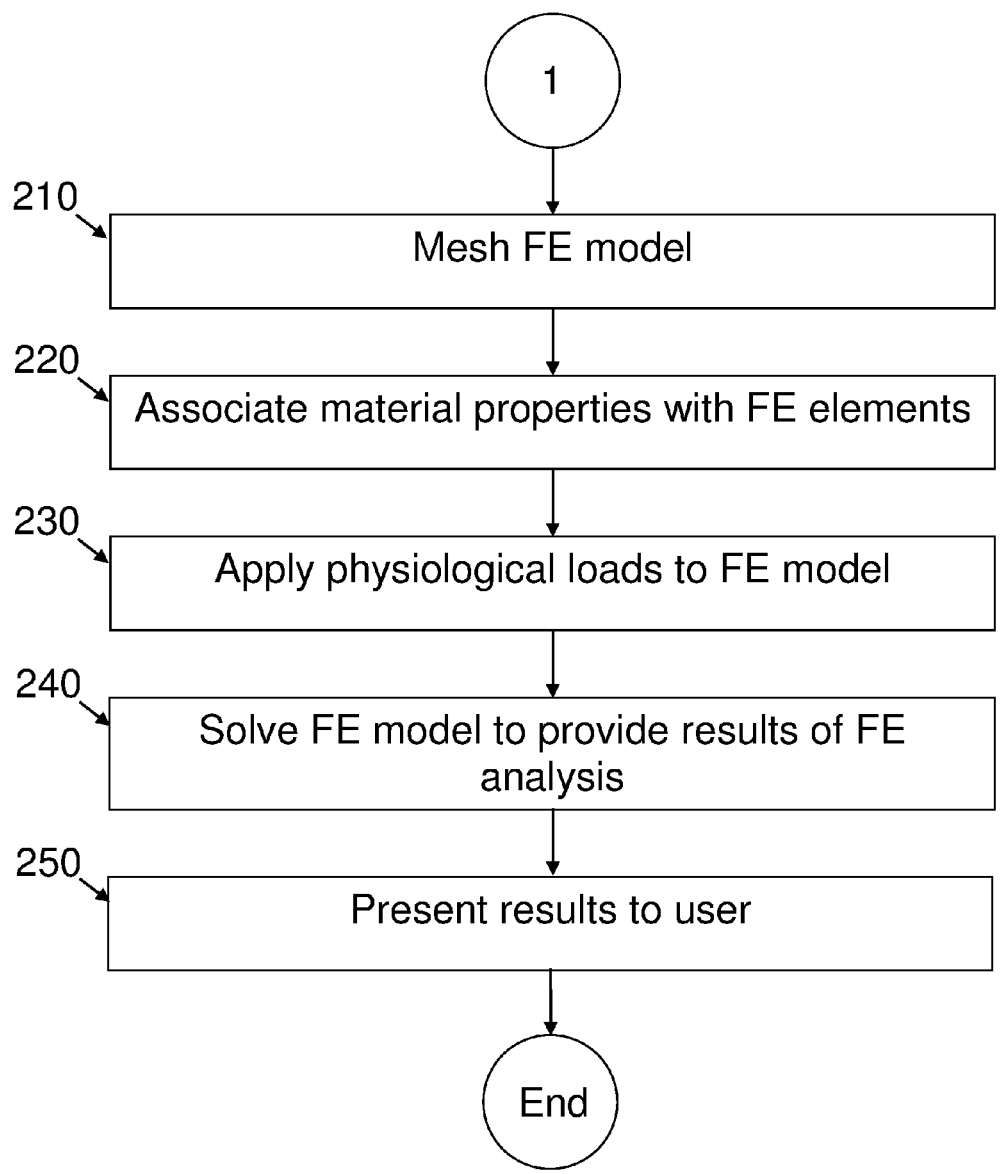

In reference to FIGS. 1 and 2, as described in more detail hereinbelow, the system executes the following steps:

1. A bone image or images is input into the system (110).
2. The image or images are analyzed to determine, in three dimensions (3D), the outer boundaries of the bone (120) and the bone density and other material properties, such as anisotropic Young's modulus (130) as a function of 3D position, within the bone. For example, the 3D bone density will show the boundary between cortical and trabecular bone. This generates a full 3D solid model (140) of the bone, including the shape of its surface and information about its interior. The full 3D solid model of the bone has a smooth (not jagged) surface.
3. From the full 3D solid model, a finite element (FE) model is generated (150) ab initio. Since the 3D model has a smooth surface, the FE model also has a smooth surface, simplifying the meshing of the FE model.
4. Either at the solid model stage or at the FE model stage, parts of the bone can be removed (160, 170), implants can be added (180, 190), or both. If the removals or additions are done at the solid model stage, the modified solid model will be meshed in its entirety. If additions are done at the FE model stage, the addition can be pre-meshed and this mesh appropriately connected to the bone FE mesh.
5. The FE model is meshed (210), using p-FEs.
6. Each FE is given material properties (220). The material properties, such as bone density, can be functions of 3D position within the bone.
7. The FE mesh is loaded (230)—physiological loads are applied to the p-FE mesh.
8. The loaded model is solved (240).
9. Results are presented to the user (250).

Steps 2, 3, 5, 6, 7 and 8 are fully automatic, requiring no user intervention.

Step 1 requires the user to input to the system, via the handheld device, sufficient information to uniquely identify the bone image or images to be used.

At step 4, the user needs to input to the system the desired modifications to be made. If bone is to be removed, the user needs to input the sections of bone to be removed, preferably via touching the appropriate parts of an image on a screen. Other methods of identifying bone to be removed will be obvious to those skilled in the art.

If an implant or other addition is to be added, the user needs to input, as appropriate, the size, type or shape of the implant or other addition. This can be done, for non-limiting example, by typing in an identifier such as a brand name, by touching an identifier on the screen, or by sketching on an image of the bone the shape of a bone graft. Other methods of identifying sizes, shapes or types of additions to the model will be obvious to those skilled in the art.

At step 9, the user can specify the type of result to be displayed, via a menu or via typing in a result type, or by any other means known in the art of specifying a result type.

At both steps 4 and 9, the user can manipulate the image, including zooming, panning and rotating. In preferred embodiments, the user can specify and display cross-sections of an image. Cross-sections can be predetermined cross-sections (e.g., X, Y and Z planes or displacements of said planes) or can be user-defined planes. In some embodiments, the user can "step through" a bone model, FE mesh, or result by incrementally displacing a cross-section, either one step at a time or as a "movie". Many variations of the above will be obvious to one skilled in the art.

In preferred embodiments, different images can be overlaid, as appropriate.

In yet other preferred embodiments, images can be stored, either on the handheld device or elsewhere and, in some embodiments, hard copies can be made.

The key features of the simulation performed by the present system include:

1. The geometric representation of the bone and the implant is based on smooth surfaces that accurately described the actual geometry in the framework of high-order elements. A proprietary segmentation algorithm is used to ensure the smoothness of the surfaces.
2. The smooth surfaces of both the solid model of the bone and the FE model of the bone very much simplify meshing the FE model, both reducing the number of elements needed and reducing the probability of unacceptably distorted elements, thus enabling fully-automatic meshing of the FE model, which was not possible in the prior art.
3. The FE mesh of the bone is patient specific; the entire mesh is generated ab initio for each FEA, unlike prior art, where patient-specific elements were added to a non-patient-specific mesh.
4. Material properties change continuously in the FE model, so that the material properties can be inhomogeneous. The material properties are determined directly from the bone image data. The p-FE method used, described hereinbelow, enables the material properties to vary within each element, so that individual elements can be larger without losing accuracy in the results. This significantly reduces the number of FEs needed for the mesh.
5. The reduced number of FEs enable solution of the model in timescales short enough that the system can be used in a clinical setting, something that was infeasible in the prior art.
6. In addition to the empirically based inhomogeneous isotropic material model above, micro-mechanics based inhomogenous orthotropic material properties can also be determined and used in simulations.
7. The numerical error of the simulation is automatically monitored, so the results are within a verified numerical error.
8. The methods described herein have been verified. For example, they have been shown to predict very well the mechanical response of femurs affected by metastatic tumors, including accurate predictions of the risk of fracture.
9. The methods described herein are robust; uncertainty in the quantification of material properties and uncertainty in the loading boundary conditions results in small errors in the results.

It should be noted that, unlike in the present system, where extensive verification has been done (see hereinbelow), in the prior art, there does not appear to have been any verification, either to compare the results against physical tests, or to calculate, internally, an estimate of the numerical error of the solution and ensure that this estimate of the numerical error is within a verified numerical error. Such verification can enable evaluation of the accuracy of the solution by a non-expert.

The overall method is automatic, reducing the time needed for the entire simulation process, as human intervention typically significantly increases simulation time. A fast convergence rate in the solver is achieved by increasing the polynomial degree (p) of the shape functions in the FE simulation so numerical errors are controlled and minimized.

The FE results, as discussed hereinbelow, were validated by experiments on a cohort of 17 healthy fresh frozen femurs, 12 fresh frozen femurs with metastatic tumors and 7 metatarsal bones. In each case, strains, displacements and fracture loads were compared between the experimental results and the FE simulations. Part of the validation process was performed in a double-blind manner by two different research institutes to avoid any bias. Overall, the FE analyses show excellent predictive capabilities.

In the present invention, p-FEs are used, rather than the more usual h-FEs.

The High-Order Finite Element (FE) Method

In FE analyses, finite dimensional subspaces that approximate the exact solution are constructed by a FE mesh, polynomial degrees assigned to the elements, and mapping functions. The basic concept of the FE method is the subdivision of the domain into components of simple geometry called elements. The response of each element is expressed in terms of a finite number of degrees of freedom characterized by the values of unknown constants that multiply shape functions. The FE error is reduced as the FE space is hierarchically enlarged. This is denoted by extension. The main difference between the two extension methods (known as h- and p-methods) lies in the enrichment of the function space. The h-extension method enlarges the FE space by mesh refinement using the same shape functions, whereas in the p-extension method the FE space is enlarged using successively higher-order polynomial shape functions, keeping the mesh fixed.

High-order FE method (p-FEM) implementation uses a hierarchical set of basis functions, which can increase to a required polynomial degree to attain a so-called convergent solution. A faster convergence rate compared to h-version is achieved by increasing the polynomial degree (p) of the shape functions, thus enabling control of the numerical errors much more easily (inherent control of the numerical approximation error). In p-FEMs larger elements with large aspect ratio can be used, and yet considerably faster convergence rates can be obtained compared to their h-FEM counterparts. Material properties are evaluated at many points within an element that allows a precise evaluation of bone high heterogeneity. The aforementioned advantages of the p-version were utilized to develop a systematic method toward p-FE simulations of the femur.

Bone Geometry and Mesh Generation Based on Bone Images

The method for bone geometric representation used herein provides: (a) An accurate description of the bone geometry. (b) Generation of a smooth surface to the bone model. (c) A reduction in the time required to construct both geometry and mesh. (d) Full integration with material property assignment.

An accurate description of the bone geometry is achieved by using blending function techniques.

Figure 3:
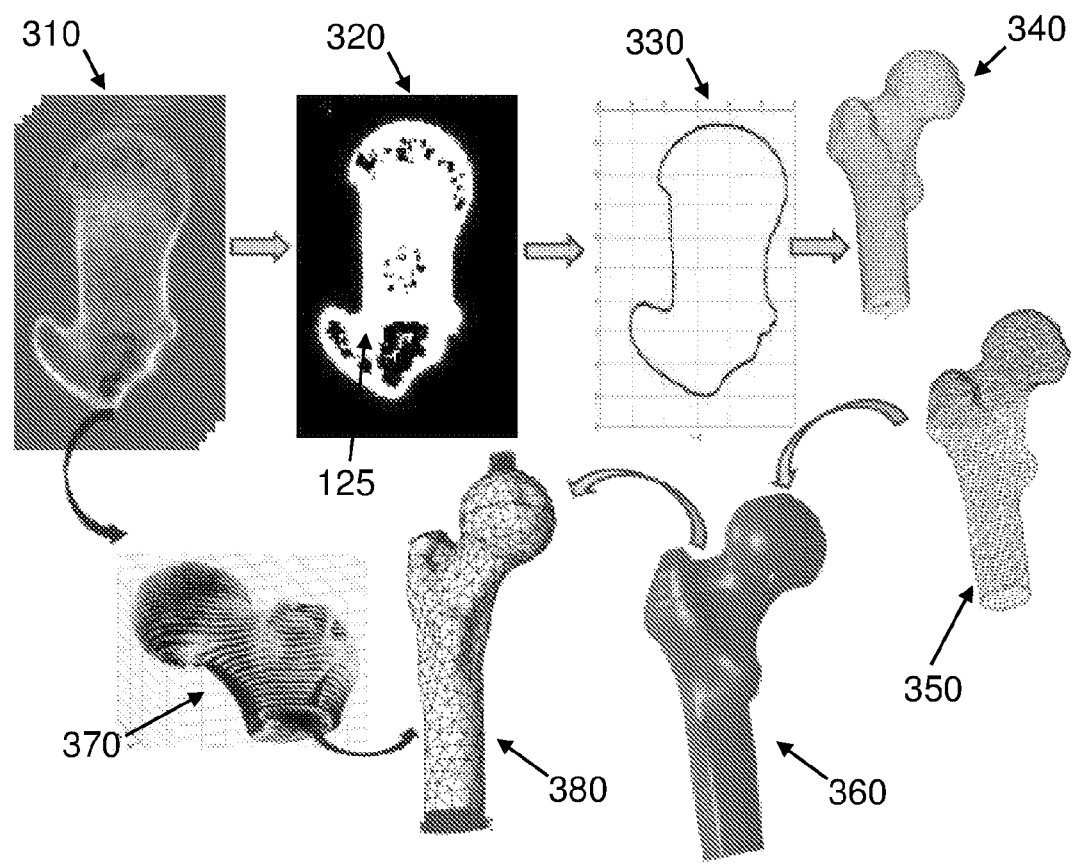
FIG. 3 schematically illustrates the process of creating a FE model from the images, the process of generating material properties for the bone, and of applying the material properties to the FE model.

In reference to FIG. 3, in the method used herein, bone image (310) files preferably in the DICoM format, preferably CT images, are imported into the system from the CT scanner or from a database. Each file represents a section of the bone having a specific thickness. Each image (110) undergoes an automatic boundary detection process (320), based on apparent density. Areas where the density is greater than a user-specified value (325, white) are deemed to be bone. Typically, the user-specified value will be a Hounsfield unit (HU) value.

In the process, the scans are first transformed into binary images in which nonzero pixels belong to the bone (325) and the value 0 is assigned to pixels representing the background (320, shown as black in the figure). Exterior (330), interface and interior boundaries are traced and x-y arrays are generated, each representing different boundaries for each slice.

In addition to the geometrical representation of the bone, the outer boundaries (330) are used to identify the pixels needed for the material property evaluation (370). Following boundary detection, the x-y-z arrays representing the bone surface are manipulated by a 3D smoothing algorithm. This algorithm applies a 3D spherical filter that calculates the new location of each point in a specific slice using data from other slices around it. Then a 2D averaging filter which considers only points from a specific slice is used for noise reduction. To complete the smoothing process, a cubic or B-spline interpolator is generated through the data points. The final output is a smooth point cloud (340) representing bone's surface. The point cloud is converted, via 3D splines (350) through the points of the point cloud into a surface or solid model (360) composed of a few patches.

The solid model of the bone is saved and imported into the p-FE code and meshed (380) using an auto-mesh option by high-order tetrahedral elements.

The material properties such as bone density and bone Young's modulus, as a function of 3D position within the bone (370), determined as described herein below, are applied to the elements in the FE mesh.

Bone Material Properties Based on Image Data

Material properties of the bone vary with position within the bone. One embodiment of a method of determining the properties comprises the substeps disclosed herein.

1. Segmentation

Segmentation is performed as described hereinabove, to generate a 3D image (220) in which bone pixels in the region of interest are identified. All pixels different from zero and surrounded by the outer boundary are taken into account. A 3D array stores each pixel's location (Row, Column and Slice Number), and its HU.

2. Noise Reduction by Boundary Correction and Moving Average

Artifacts in the image, such as CT artifacts, can seriously damage image quality. When performing a CT scan for the human femur, the partial volume effect (PVE) is particularly noticeable in the surroundings between the bone and the soft tissue. To minimize partial volume artifacts, a correction algorithm is applied as part of the image processing procedure. After the boundary detection process, in each image, the area around each boundary pixel is scanned and the maximum HU number is identified. This HU number is then assigned to all pixels affected by the PVE at a predefined distance from the boundary pixel. Noise reduction is then completed by moving average filtering. The moving average algorithm is applied to average the HU data in each voxel based on a pre-defined cubic volume of 3×3×3 voxels around it. These values reduce the numerical errors caused by unsmoothed material distribution.

Figures 4A, 4B:
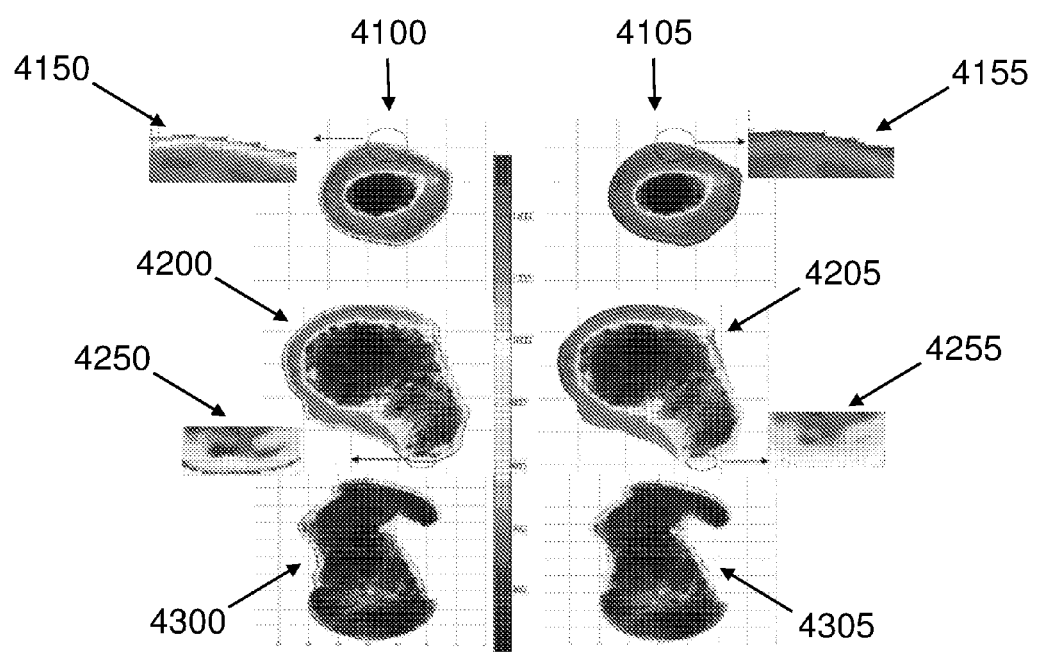
FIG. 4A-B depicts the effects of noise reduction on the bone density.

Noise reduction by boundary correction and moving average in typical CT images is demonstrated in FIG. 4A-B. FIG. 4A shows typical CT scan images of a human femur (4100, 4200, 4300), at three different levels in the femur. Close-ups of the edge of the femur (4150, 4250) are also shown. FIG. 4B shows the same CT scans (4105, 4205, 4305) and the same close-ups (4155, 4255) after boundary correction and noise reduction. The colors show the density, with red representing the highest density and blue the lowest density.

In FIG. 4A, a section (4150) of the upper edge of the uppermost bone slice (FIG. 4A, 4100) is shown before boundary correction and noise reduction. FIG. 4B shows the same section (FIG. 4B, 4155) after noise reduction. In FIG. 4A, the density drops very noticeably near the edge (edge is green), whereas, after noise reduction (FIG. 4B, 4155), the bone density remains high (red) to the edge of the bone, which is physically much more reasonable. Similarly, in the close-up (FIG. 4A, 4250, FIG. 4B, 4255) of the central slice (FIG. 4A, 4200, FIG. 4B, 4205), the close-up (FIG. 4A, 4250) clearly shows that the density appears to be very low (blue) near the edge of the bone, whereas, after noise reduction, the close-up (FIG. 4B, 4255) shows that the bone edge regions are more dense (yellow) than the central region (blue, low density) and that the density remains nearly constant to the edge of the bone. In the lowest slice (FIG. 4A, 4300, FIG. 4B, 4305), there are more extensive regions of high density (red) near the edge of the bone after noise reduction (FIG. 4B, 4305) than there were before noise reduction (FIG. 4A, 4300).

Accounting for the Spatial Material Property Dataset

The 3D array generated in the previous steps is manipulated to construct a file of x, y, z coordinates and their associated HU values.

Material properties can be isotropic or orthotropic. In isotropic materials, the properties may be different at different points within the material, but the material properties at any point are the same in all directions; it is possible to say that, at a given point, the value of, for non-limiting example, the Young's modulus is, for non-limiting example, 200 MPa.

For anisotropic materials, the material properties at a given point differ in different directions so that, for non-limiting example, the bone has a greater Young's modulus parallel to its longitudinal than the Youn'g modulus perpendicular to that axis.

Isotropic Material Properties

For an inhomogeneous isotropic material model, Young's modulus $E(x, y, z)$ and Poisson's ratio need to be determined.

Figure 5:
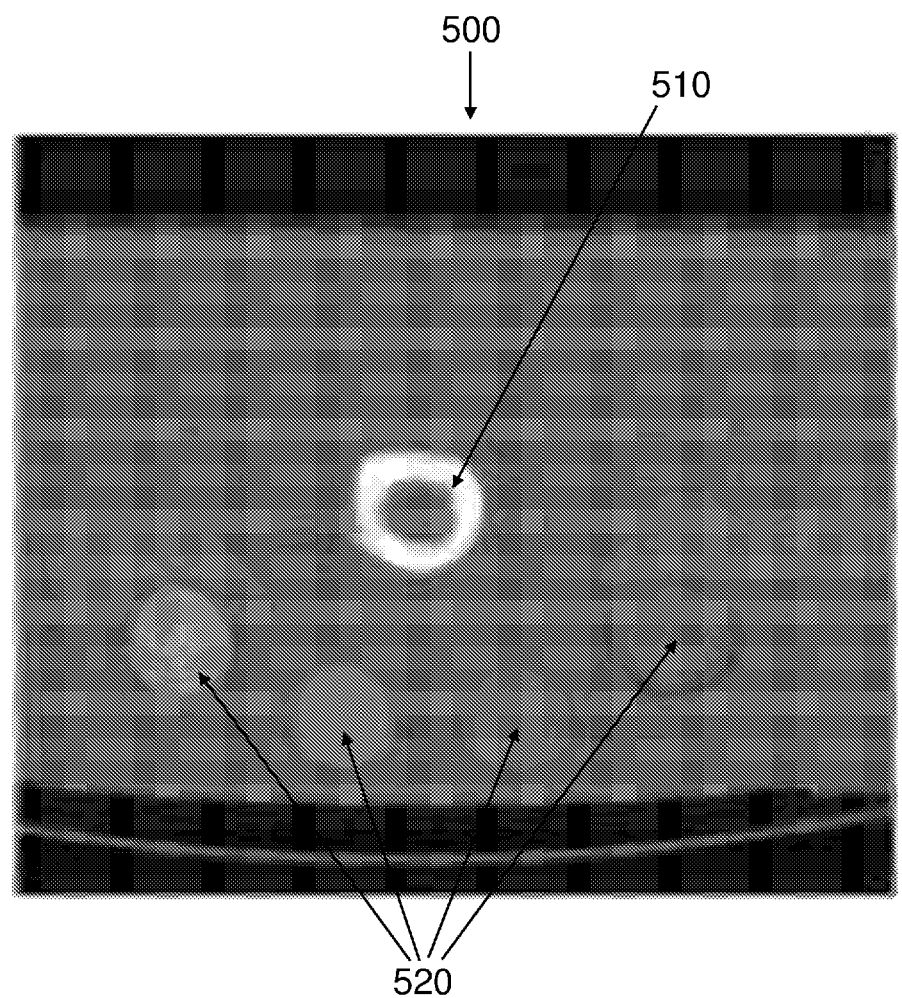
FIG. 5 depicts an image of a bone, including the phantoms used for normalizing the conversion of image density to bone density.
Figure 6:
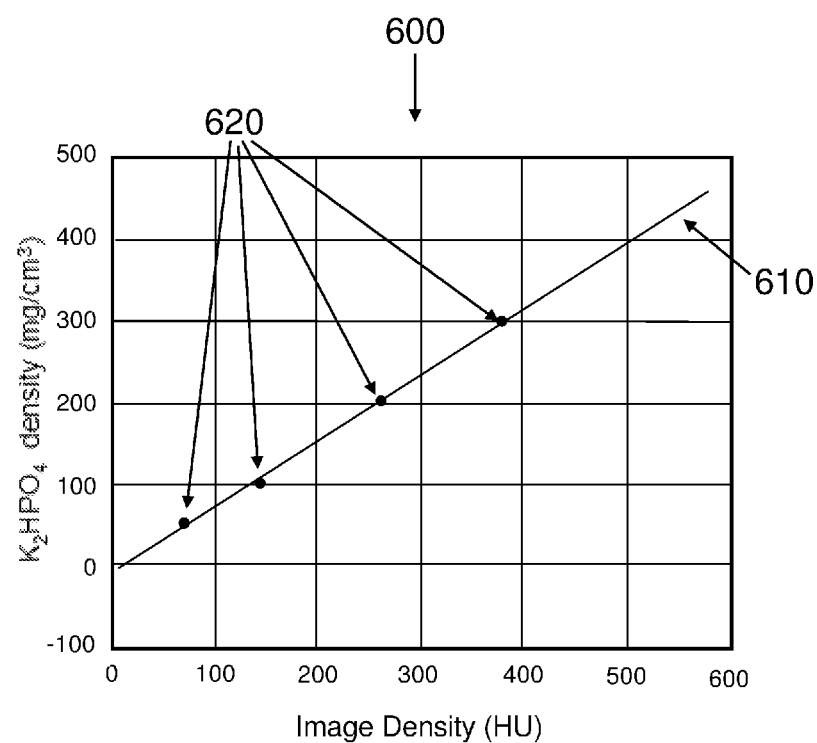
FIG. 6 illustrates the correlation of image density and phantom density.

The pointwise Young's modulus can be determined from CT scan images as follows: Five calibration phantoms (with different concentration of $K_2HPO_4$ ranging from 0 to 300 mg/cm$^3$) are placed around the bones during the CT scan. FIG. 5 shows a CT scan image (500) of a bone (510) surrounded by the phantoms (520). As shown in FIG. 6, a linear relationship (610) provides a good correlation between the densities of these phantoms, (in Hounsfield Units—HUs) and the bone ash density $\rho_{ash}$. In FIG. 6, the data are shown as circles (620) and the line (610) is the best-fit line to the data. The phantom density $\rho_{K_2HPO_4}$ is associated with the bone ash density $\rho_{ash}$ according to the equation $$\rho_{ash} [gm/cm^3] = 0.877 \times 1.21 \times \rho_{K_2HPO_4} + 0.08 \quad (1)$$

And, from $\rho_{ash}$, the Young's moduli of the cortical bone, $E_{Cort}$, and the trabecular bone, $E_{Trab}$ are determined, according to $$E_{cort} = 10200 \rho_{ash}^{2.01} \text{ [MPa]} \quad \rho_{ash} \geq 0.486 \quad (2)$$

$$E_{trab} = 2398 \text{ [MPa]} \quad 0.3 < \rho_{ash} \geq 0.486 \quad (3)$$

$$E_{trab} = 33900 \rho_{ash}^{2.2} \text{ [MPa]} \quad \rho_{ash} \leq 0.3 \quad (4)$$

These relationships were found to provide an excellent match between the p-FE analyses and experiment for the proximal femur.

Micro-Mechanics-Based Orthotropic Material Properties

As described above, an orthotropic material has at least 2 orthogonal planes of symmetry, with the material properties differing between the planes. Such materials require 9 independent variables (i.e. elastic constants) in their constitutive matrices. Several assumptions and a more sophisticated approach have to be applied than for an isotropic material. A continuum micro-mechanics-based (MM-based) model may be applied to, for example, the QCT scans to determine (non-empirical) relations between orthotropic elasticity tensor components and HU (see works of Hellmich and co-workers).

In some embodiments, additional scans, such as X-ray vector radiography (XVR) are taken of the bone. From the XVR data, orthotropic material properties can be found. Other methods of determining orthotropic material data are known in the art.

Material Property Assignment to the p-FE Model

The computation of Young's modulus as a function of positions, $E(x, y, z)$, at each integration point (Gauss points, 512 points of interest (POI) for a tetrahedral p-element) is performed as follows. The Young's modulus value at every Gauss point is computed using a weighted point average (WPA) method directly from the material dataset file: eight vertices of a cube in which the Gauss point is located are identified and the value at the Gauss point is computed by its relative distance from the vertices. For CT-scans with high enough resolution, the algorithm is more efficient if the value at the Gauss point is determined according to its closest point in the CT scan, with very little influence on the results.

Figure 7:
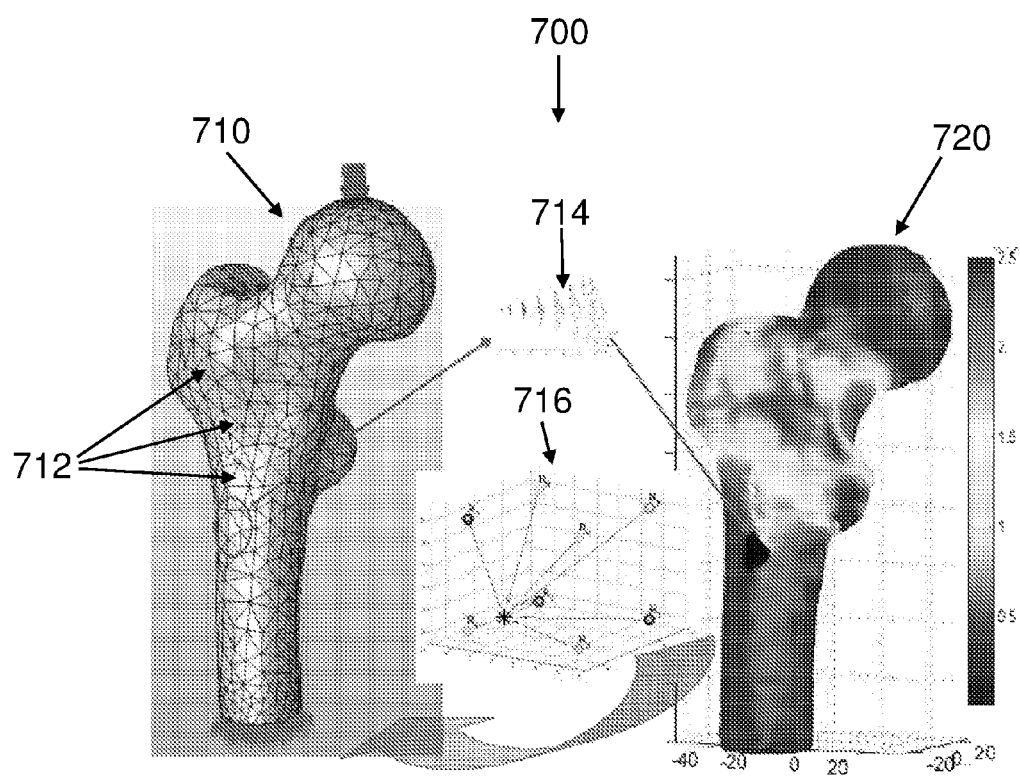
FIG. 7 schematically illustrates an embodiment of a process of assigning material properties to the FE model from the material properties of the solid bone model.

FIG. 7 illustrates an embodiment of a method (700) of assigning Young's modulus values to Gauss points (POI). In this method, the Young's modulus values are determined as a function of position in the bone (720). A FE mesh of the bone (710) is created, containing a plurality of elements (712). For each element (712), the locations of the Gauss points (714) are determined. For each Gauss point, the distance from the vertices (716) (where the Young's moduli are known) are calculated and a weighted average of the modulus values at these vertices is calculated. Alternatively, the Young's modulus at the vertex nearest to the Gauss point can be used.

Verification and Validation of FE Models

Figure 8:
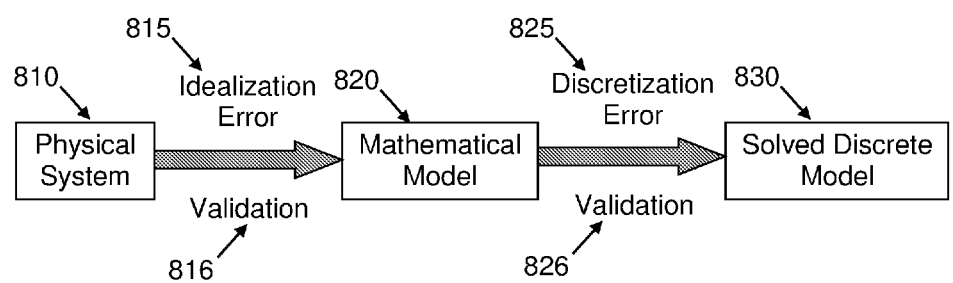
FIG. 8 schematically illustrates sources of error in the process of creating a FE model from a physical system.

As illustrated in FIG. 8, the FE process of obtaining quantitative information about a real physical system (810) includes two sources of error. The idealization error (815) is associated with the assumptions used to describe the physical system (810) by a simplified mathematical model (820) and how well the mathematical model (820) reflects the essential features of the physical system (810). These errors are due to simplifications in areas such as, but not limited to, the geometry, the boundary conditions and the material constitutive laws. In the cases of biomechanics, idealization errors (815) can be difficult to assess.

The discretization error (825) is the difference between the numerical solution (830) of the mathematical model (820) and the exact solution. It includes error due to differences between the FE mesh and the geometry of the mathematical model, error due to discretizing the material constitutive laws, and error from the numerical solver.

Discretization error (825) can be reduced and controlled by mesh refinement and/or increase of the polynomial degree (h- or p-extensions).

Idealization validation (816) and discretization validation (826) can be used to ensure that the effects of both idealization error (810) and discretization error (820) are understood and that the sizes of these errors are controlled.

In the presented method the discretization and idealization errors are estimated by an extensive processes of verification and validation (V&V), where verification is performed to ensure that the numerical error is under a specific tolerance while validation ensures that the FE analysis represents the real physical (biomechanical) response. Sensitivity analyses are an integral part of both verification and validation. Verification, validation and sensitivity analyses are mandatory for achieving a reliable solution, where a reliable solution is one in which the calculated quantities of interest correspond well to the actual physical quantities, if such were measurable.

Furthermore, for a reliable solution, it is necessary to consider all sources of error to ensure that the total error is sufficiently small.

The present invention ensures reliable solutions by having carried out an extensive series of tests, and by ensuring that the calculated quantities of interest corresponded well to the experimental observations.

V&V are evolving techniques that, if used improperly, can lead to false conclusions about a system under study. Verification must precede validation, to separate errors due to model implementation from uncertainty due to model formulation. Confidence in computational simulations is only possible if the mathematical foundation of the model has been verified and the results validated against experimental observations.

There are various measures of goodness of fit, like linear regression, normalized root mean squared error, average error and so on. Linear regression graphs used to assess the quality of the numerical analysis are very common in the literature in the field of biomechanics. A prediction model is well-calibrated if both the linear slope and correlation coefficient $R^2$ are close to 1 and the intercept close to 0.

Model Verification

All p-FE results presented herein are verified by convergence checks, keeping a fixed mesh and increasing the polynomial degree p of the approximated solution. p is increased until the relative error in energy norm is small (<5%), and the stress, strains or displacements at the points of interest converge to a given value. Such verification processes are exemplified in FIG. 9A-C.

Figure 9A:
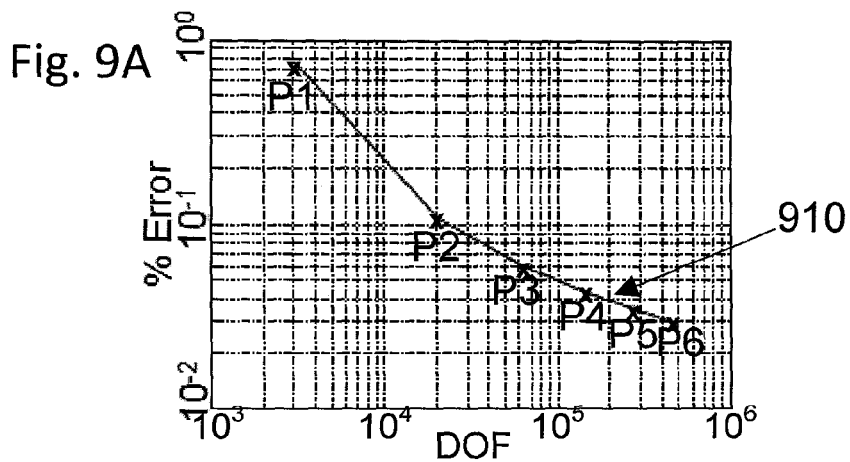
FIG. 9A-C illustrates the effect of p-FE polynomial order on convergence for a fixed FE mesh.
Figure 9B:
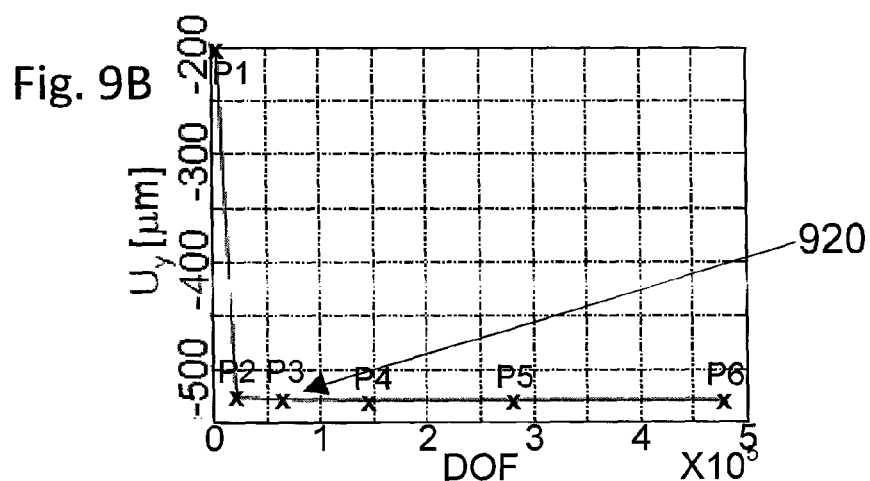
Figure 9C:
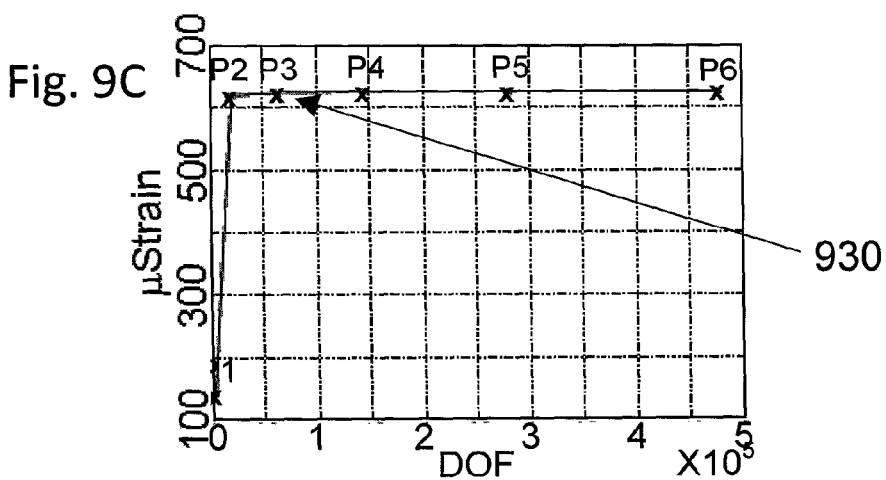

FIG. 9A shows the effect of increasing the number of degrees of freedom (DOF) on the energy norm, while FIG. 9B shows the effect of increasing the number of DOF on displacement of a specified point in a model, and FIG. 9C shows the effect of increasing the number of DOF on the strain in the 1-direction, $\epsilon_1$. The number of DOF in a model depends on the number of FEs in the model and on the polynomial degree p of the approximated solution. In the verification shown in FIG. 9A-C, the FE mesh was held fixed and the polynomial degree p was increased from 1 to 6.

When increasing p from 1 to 6 one may check the convergence in energy norm (FIG. 9A), displacements (FIG. 9B) and strains (FIG. 9C). Based on this example one can conclude that the estimated relative error in energy norm at p>4 is less than 5% (910), and the strains (930) and displacements (920) are converged beyond p=3.

Model Validation

To validate the FE results, a comparison between the p-FE predictions and experimental observations was performed. A simplified stance position loading was considered in all experiments. The verified FE models that mimic the in-vitro experiments were used for this purpose. For each FE analysis the strains and displacements at the location of the strain gauges (SGs), linear variable differential transformer (LVDT) or optical markers to measure displacement were averaged over a small area representing the area over which the measurement was extracted. Because uni-axial SGs were used in all experiments, the FE-strain component is considered in the direction coinciding with the SG direction. Tens of displacements and hundreds of strains on 29 femurs and 7 metatarsals were used to assess the validity of the p-FE simulations. Statistics were based on the standard and accepted approach of linear regression and mean error value for the prediction model. For linear regression, a perfect correlation is indicated by a unit slope, a zero intercept and a unit $R^2$.

Figure 10:
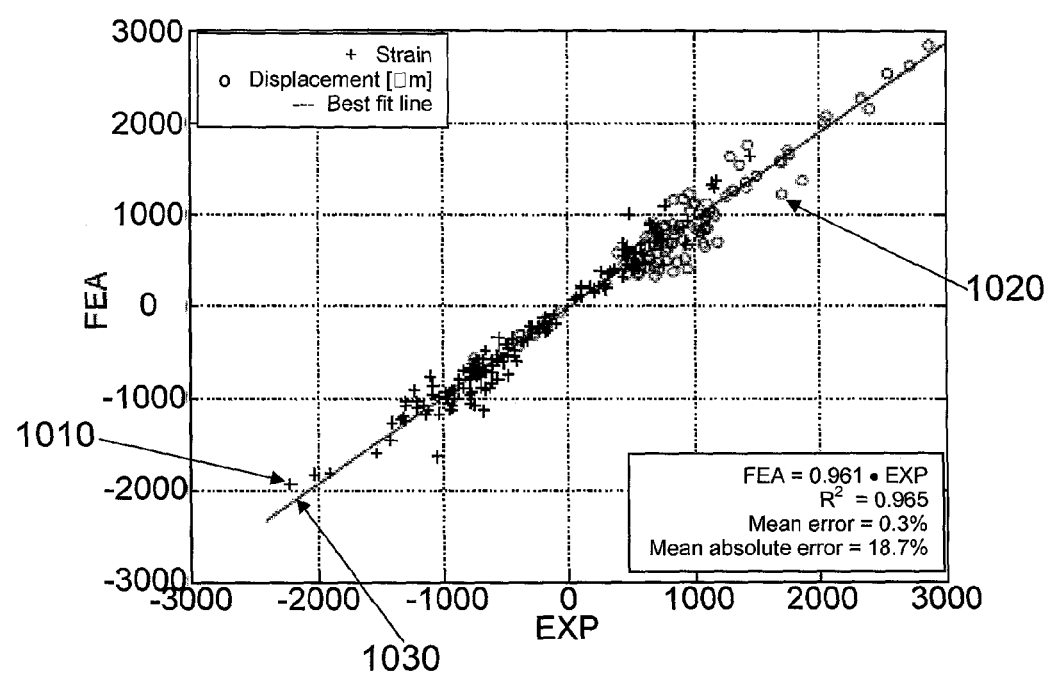
FIGS. 10, 11A-B, 12 depict a comparison of experimentally measured and FEA calculated strain and displacement data for human femurs.

The mean error and the absolute mean error are also calculated for the data. If there are N measurements, the mean error is $$\text{Mean Error} = \frac{1}{N}\sum_{i=1}^{N} 100\frac{(Exp_i - FE_i)}{Exp_i} \qquad (5)$$

and the mean absolute error is $$\text{Mean Absolute Error} = \frac{1}{N}\sum_{i=1}^{N} 100\frac{|(Exp_i - FE_i)|}{Exp_i} \qquad (6)$$

where Exp is the experimental value, FE is the calculated value and the subscript i indicates the $i^{th}$ value In FIG. 10, the pooled FE strains (1010) and displacements (1020) are compared to the experimental observations, and a best-fit line (1030) is shown. The correlation for these pooled data is good, with $R^2=0.965$.

Figure 11A:
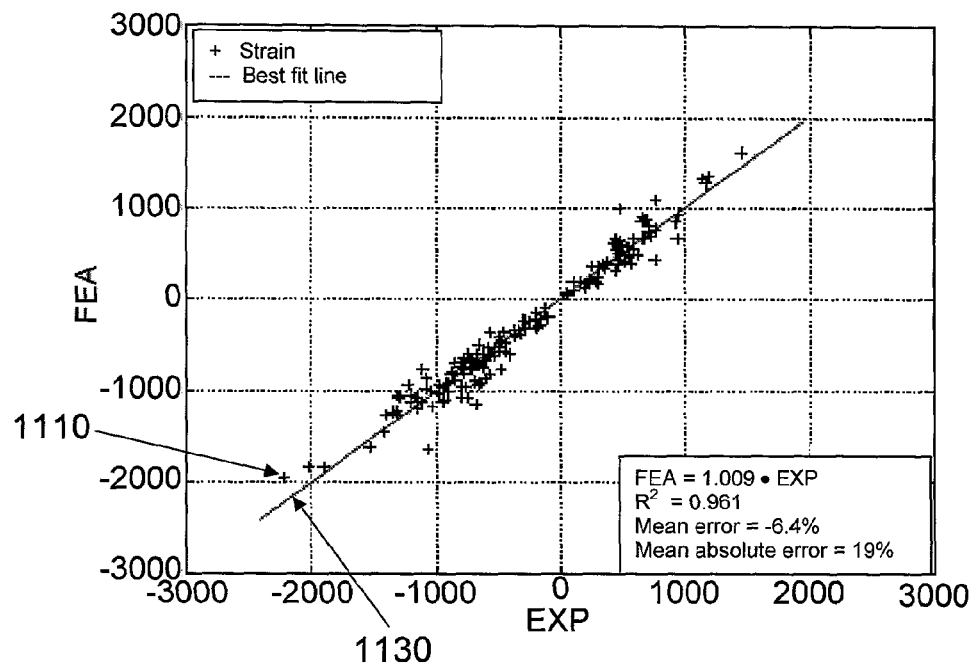
Figure 11B:
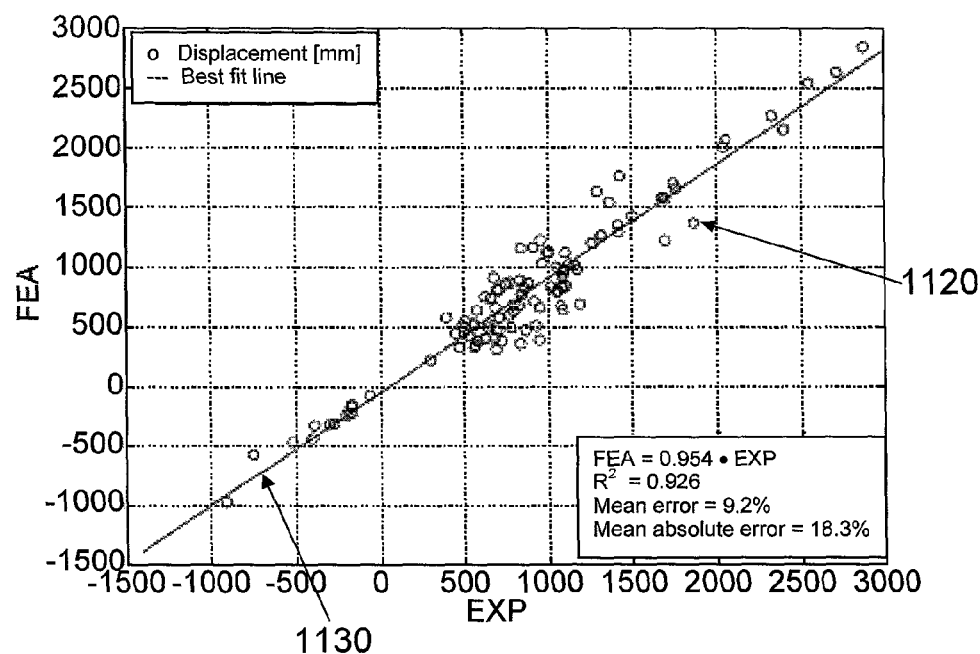

In FIG. 11A-B, we consider the predicted strains alone (FIG. 11A, 1110) and predicted displacements (FIG. 11B, 1120) alone, with best-fit lines (1130) shown for both. Again, the correlation is good, with $R^2=0.961$ for the strains (1110) and $R^2=0.926$ for the displacements. The smaller $R^2$ for the displacements is unsurprising, because there are fewer displacement data.

Figure 12:
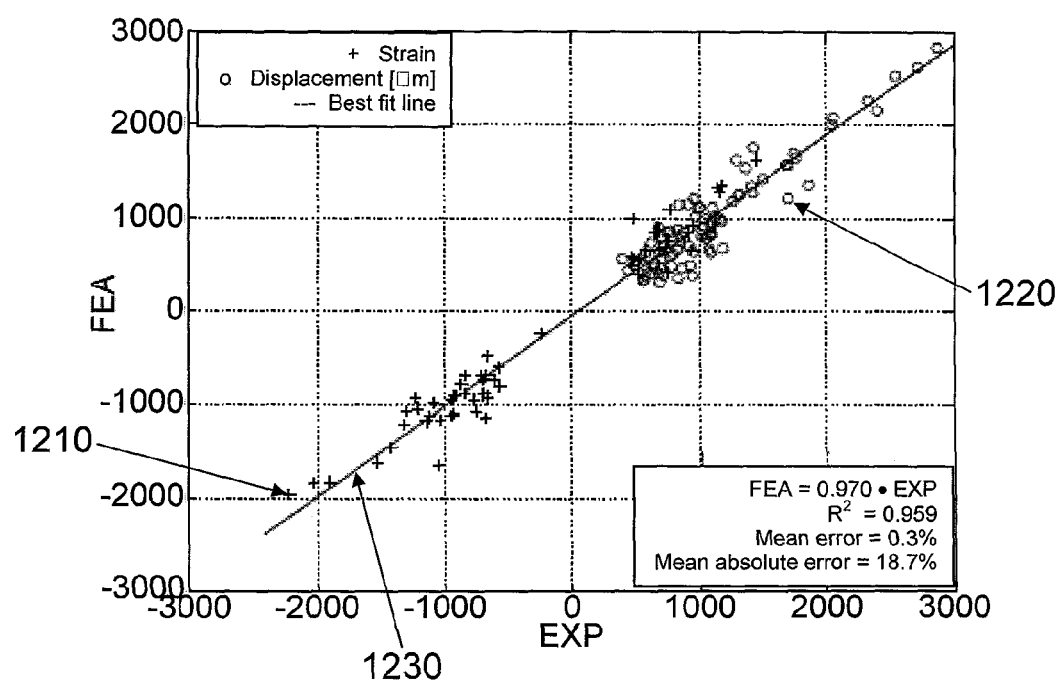

FIG. 12 shows only the results from the 12 femurs used in the blind comparison, with all the data from both research institutes plotted. The strains (1210, crosses) and displacements (1220, circles) are shown, as is the best-fit line (1230). $R^2=0.959$ for the double-blind data.

Overall, the FE results are considered to be in excellent agreement with the experimental measurements, with all comparisons showing high $R^2$.

Figure 13:
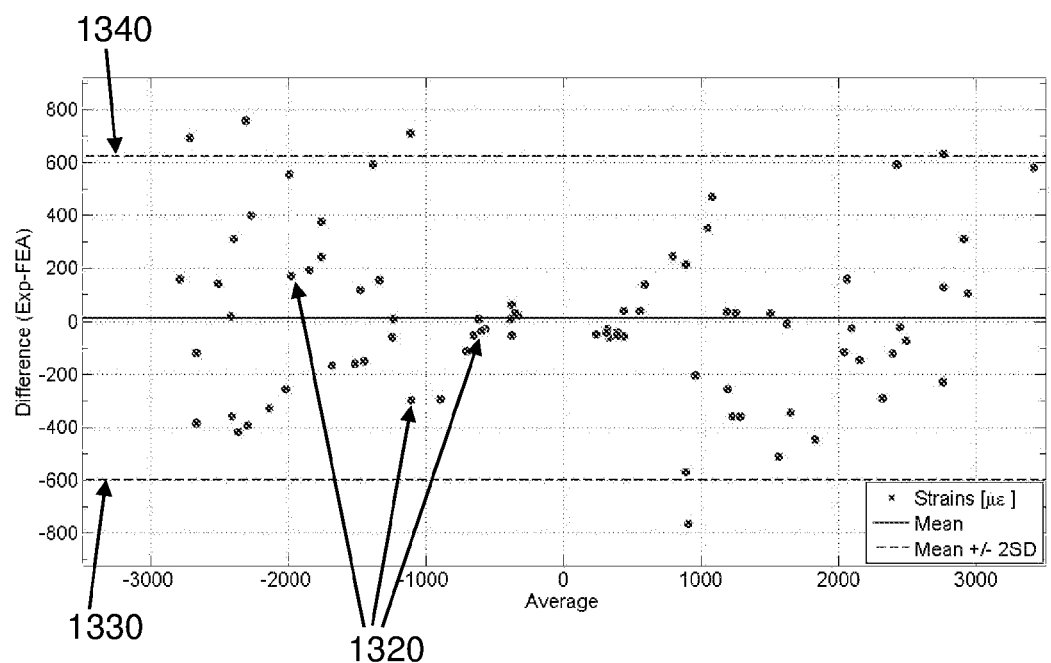
FIG. 13 depicts the difference between experimentally measured and FEA calculated strain and displacement data for human femurs.

FIG. 13 shows the error in the strain as a function of the strain. The data (1320) appear to be randomly distributed; there is little sign of systematic errors, as indicated by the symmetry of the distribution; the +2 standard deviation line (1340) is very close to the absolute value of the −2 standard deviation line (1330).

Example 1

The methods were examined on different fresh frozen bones with different CT resolutions. To compare between both methods and to assure model's accuracy, several measurements were taken and compared to the geometrical model. The comparison of the outer contour dimensions generated from CT data and the real femur shows a maximum error of 2% (usually less than 1 mm which is in the range of the CT resolution and the measurements tool error).

Example 2

Validation of the material properties was performed by applying a load of 1000 N to a section of a thawed fresh-frozen human femur. The femur was scanned by quantitative computed tomography (QCT) and thereafter loaded (in vitro experiments) by the quasi-static load. QCT scans were manipulated to generate a high-order FE bone model with distinct cortical and trabecular regions having inhomogeneous isotropic elastic properties with Young's modulus represented by continuous spatial functions. Sensitivity analyses were performed to quantify parameters that have the most influence on the mechanical response. FE results were compared to displacements and strains measured in the experiments.

Figure 14:
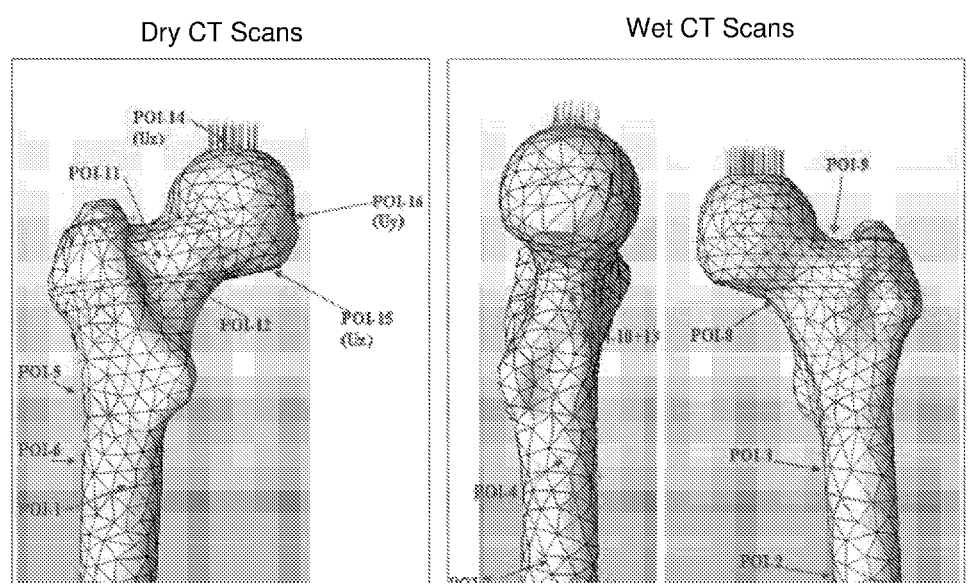
FIG. 14 illustrates the location of strain and displacement gauges on a human femur.
Figures 15A, 15B, 15C, 15D:
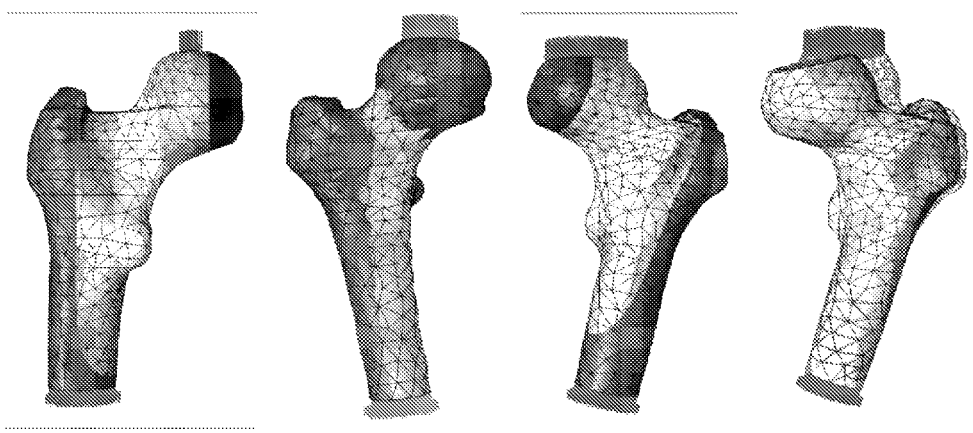
FIG. 15A-D illustrates the positions of a human femur at the start of loading, illustrating the 0°, 7°, 15° and 20° angles of the femur.

After defrosting, soft tissue was removed from the bone and the bone was degreased with ethanol. The proximal femur was cut and fixed concentrically into a cylindrical sleeve by six bolts and a PMMA substrate and was scanned in two different environments. QCT scans were performed using a Phillips Brilliance 64 CT (Eindhoven, Netherlands) with the following parameters: 120 kVp, 250 mAs, 1.25 mm slice thickness, axial scan without overlap, and pixel size of 0.5176 mm (512 pixels covering 265 mm field size). In the wet scan ($CT_{wet}$) the bone was immersed in water. Five burettes (calibration phantoms) containing different concentrations of $K_2HPO_4$ ranging from 0 to 300 mg/cm$^3$ were placed in the tub close to the bone. The aim of this scan was to simulate in situ conditions and reduce beam hardening effects. Following the QCT, strain-gauges (SGs) were bonded using M-Bond 200 cyanoacrylate adhesive, as shown in FIG. 14. A second scan ($CT_{dry}$) was performed with the bone exposed to air. This enables identification of the exact location of the SGs. Mechanical experiments started 8 h after bone mounting, long enough for the PMMA to cure, and lasted for 20 h (bone was constantly hydrated). Two p-FE models were generated based on QCT scans. Bone was loaded by a load controlled machine (Instron 5500R). Two linear variable differential transformer (LVDT) measured the femur head vertical and horizontal displacements (core placed on femur's head) (FIG. 14, POI 14-16). Thirteen uni-axial SGs (Vishay CEA-06-062UR-350) with 1.6 mm active length (FIG. 14, POI 1-13) were bonded on the proximal femur at the inferior and superior parts of the femur neck and on the medial and lateral femur shaft. SGs, load-cell and the LVDT outputs were recorded. Loading was from the top of the femur (arrows). The experiments simulate a simple stance position configuration in which the femur is loaded through its head while it is inclined at four different angles, as shown in FIG. 15A-D (0° (FIG. 15A), 7° (FIG. 15B), 15° (FIG. 15C) and 20° (FIG. 15D)).

The geometric representation, material properties evaluation and analysis results were compared. p-FE simulations that mimic the experiments were performed and results were compared to experimental observations.

Representative results are shown in Table 1, where the POI are the locations of the strain and displacement gauge, as shown in FIG. 14.

TABLE 1

Typical strains (and difference in percentage) at 1000N computed by p-FEs and experimental measurements.

| | POI 10 [strain] | | | POI 12 [strain] | | |
| --- | --- | --- | --- | --- | --- | --- |
| Angle | Computed by p-FEs | Experimental Measurement | Difference | Computed by p-FEs | Experimental Measurement | Difference |
| 0° | −1065 | −880 | 21% | −254 | −299 | −5% |
| 7° | −712 | −776 | −8% | −301 | −306 | −2% |
| 15° | −630 | −750 | −16% | −293 | −287 | 2% |
| 20° | −572 | −720 | −21% | −289 | −284 | 2% |

Difference (%) = 100 (FEA − Exp)/Exp.

The invention claimed is:
1. A computer-implemented method for providing finite element analysis (FEA) of at least a portion of at least one bone in a patient, said method comprising:
   a. providing at least one image of at least a portion of said bone;
   b. calculating material properties of said bone as a function of three dimensional (3D) position within said bone from density of said bone as a function of 3D position within said bone via empirically-determined material properties correlated to density, said density determined from at least one property of said image of said bone;
   c. generating an analyzable model using steps of:
      i. generating by an automatic algorithm from said image a solid model of said at least a portion of said at least one bone by steps of: identifying the boundaries of said bone in said image, said boundary identification via edge detection software; smoothing said boundaries; generating a point cloud model of said boundaries; generating spline curves through points in said point cloud; and generating a solid model through said spline curves;
      ii. automatically generating, from said solid model, a finite element (FE) mesh of said at least a portion of said at least one bone, said FEs being high-order finite elements (p-FE) having smooth surfaces;
      iii. applying a noise reduction algorithm by boundary correction and moving average for each said FE in said p-FE mesh;
      iv. for each said FE in said p-FE mesh, setting said material properties of said FE according to said material properties of said bone at said 3D position;
      v. applying boundary conditions to at least one said FE in said FE mesh;
   d. solving said analyzable model, thereby generating a solved model; and
   e. providing at least one result from said solved model
   wherein said steps of providing said bone image ensure that said solved model is patient-specific;
   wherein said steps of generating said point cloud and generating said spline curves enable the surface of said solid model to be smooth, thereby enabling the surface of said FE model to be smooth, and further wherein said steps of generating said FE mesh of p-FE enable said FEs to have heterogeneous material properties, thereby reducing the number of FEs in said FE mesh; and
   further wherein said steps of determining material properties comprise additional steps of identifying the cortical-trabecular boundary of said bone, of identifying voxel values of Hounsfield unit (HU)>475 (bone ash density $\rho_{ash}$>0.486 g/cm$^3$) as said cortical bone and of identifying voxel values of HU<475 ($\rho_{ash}$<0.486 g/cm$^3$) as said trabecular bone.

2. The computer-implemented method of claim 1, additionally comprising steps of generating said at least one image by a method selected from a group consisting of: computed tomography (CT), X-ray vector radiography (XVR), magnetic resonance imaging (MRI), positron emission tomography (PET), and any combination thereof.

3. The computer-implemented method of claim 1, additionally comprising steps of providing a graphical user interface (GUI) for display of material related to said image, said outer boundary, said analyzable model, said solved model, said results and any combination thereof.

4. The computer-implemented method of claim 3, additionally comprising at least one selected from a group consisting of: displaying an image of at least a portion of said at least one bone; manipulating said bone image; displaying an image of said solid model; manipulating said solid model image; modifying said solid model; displaying an image of said FE mesh; manipulating said FE image; modifying said FE mesh; displaying an image of said bone density; manipulating said density image; modifying said density; displaying said member of said group consisting of loads and constraints; modifying at least one member of said group consisting of loads and constraints; displaying said results of said solution; and manipulating said display of said results.

5. The computer-implemented method of claim 1, wherein said empirically-determined material properties are inhomogeneous.

6. The computer-implemented method of claim 1, wherein said steps of applying at least one boundary condition comprises applying at least one member of a group consisting of loads and constraints.

7. The computer implemented method of claim 1, additionally comprising steps of generating said results by analyzing said solved model.

8. The computer implemented method of claim 7, wherein said analyzing of said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

9. A computer-implemented system for providing finite element analysis (FEA) of at least a portion of at least one bone in a patient, said system comprising:
   a. at least one processor configured to:
      i. input an image of at least a portion of at least one bone in a patient;
      ii. calculate material properties of said bone as a function of three dimensional (3D) position within said bone from density of said bone as a function of 3D position within said bone via empirically-determined inhomogeneous isotropic material properties correlated to density, said density determined from at least one property of said image of said bone;
      iii. generate an analyzable model, said generation comprising:
         1. generation by an automatic algorithm, from said image, of a solid model of said at least a portion of said at least one bone by identifying the boundaries of said bone in said image, said boundary identification via edge detection software; smoothing said boundaries; creating a point cloud model of said boundaries; generating spline curves through points in said point cloud; and generating a solid model through said spline curves;
         2. automatic generation, from said solid model, of a finite element (FE) mesh of said at least a portion of said at least one bone, said FEs being high-order finite elements (p-FE);
         3. for each said FE in said p-FE mesh, setting of said material properties of said FE according to said material properties of said bone at said 3D position; and
         4. application of at least one member of a group consisting of loads and constraints to at least one said FE in said FE mesh;
      iv. solve said analyzable model, thereby generating a solved model; and
   b. a device configured to display at least one result from said solved model wherein said bone image enables said solved model to be patient-specific;

wherein said point cloud and spline curves enable the surface of said solid model to be smooth, and further wherein said use of said p-FEs enables said FEs to have heterogeneous material properties and reduce the number of FEs in said FE mesh;

further comprising a step of identifying said cortical-trabecular boundary of said bone, said cortical bone being identifiable as having voxel values of Hounsfield unit (HU)>475 (bone ash density $\rho_{ash}$>0.486 g/cm$^3$) and said trabecular bone being identifiable as having voxel values of HU<475 ($\rho_{ash}$<0.486 g/cm$^3$).

10. The computer-implemented system of claim 9, wherein said at least one image is generable by a method selected from a group consisting of: computed tomography (CT), X-ray vector radiography (XVR), magnetic resonance imaging (MRI), positron emission tomography (PET), and any combination thereof.

11. The computer-implemented system of claim 9, wherein a graphical user interface (GUI) is provided for display of material related to said image, said outer boundary, said analyzable model, said solved model, said results and any combination thereof.

12. The computer-implemented system of claim 11, additionally configured to perform at least one selected from a group consisting of: display an image of at least a portion of said at least one bone; manipulate said bone image; display an image of said solid model; manipulate said solid model image; modify said solid model; display an image of said FE mesh; manipulate said FE image; modify said FE mesh; display an image of said bone density; manipulate said density image; modify said density; display said member of said group consisting of loads and constraints; modify at least one member of said group consisting of loads and constraints; display said results of said solution; and manipulate said display of said results.

13. The computer-implemented system of claim 9, wherein said empirically-determined material properties are inhomogeneous.

14. The computer-implemented system of claim 9, wherein applying said at least one boundary condition comprises applying at least one member of a group consisting of loads and constraints.

15. The computer implemented system of claim 9, additionally configured to generate said results by analyzing said solved model.

16. The computer implemented system of claim 15, wherein said analysis of said solved model comprises locating regions in said solved model in which a measure of strains/stresses or any function of these are greater than a predetermined self-determined maximum; locating regions in said solved model where fractures have occurred; locating regions in said solved model in which movement is greater than a predetermined maximum; and any combination thereof.

* * * * *